United States Patent
Williams et al.

(10) Patent No.: US 9,057,684 B2
(45) Date of Patent: Jun. 16, 2015

(54) GAMMA RAY IMAGING SYSTEMS AND METHODS

(71) Applicant: The Arizona Board of Regents on behalf of the University of Arizona, Tucson, AZ (US)

(72) Inventors: John G. Williams, Tucson, AZ (US); Aaron M. Farber, Tucson, AZ (US)

(73) Assignee: The Arizona Board Of Regents On Behalf Of The University Of Arizona, Tucson, AZ (US)

( * ) Notice: Subject to any disclaimer, the term of this patent is extended or adjusted under 35 U.S.C. 154(b) by 188 days.

(21) Appl. No.: 14/063,611

(22) Filed: Oct. 25, 2013

(65) Prior Publication Data

US 2014/0301535 A1    Oct. 9, 2014

Related U.S. Application Data

(60) Provisional application No. 61/808,881, filed on Apr. 5, 2013.

(51) Int. Cl.
*G01N 23/20* (2006.01)

(52) U.S. Cl.
CPC .............................. *G01N 23/20066* (2013.01)

(58) Field of Classification Search
CPC ... G01T 1/295; G01N 23/20066; G01N 23/22
USPC ...................................................... 250/363.01
See application file for complete search history.

(56) References Cited

U.S. PATENT DOCUMENTS

| 7,541,592 B2 | 6/2009 | Gottesman |
| 7,863,567 B1 | 1/2011 | Hynes et al. |
| 8,153,986 B2 | 4/2012 | Mihailescu et al. |

(Continued)

FOREIGN PATENT DOCUMENTS

| EP | 1272108 A2 | 1/2003 |
| EP | 2340445 A2 | 7/2011 |

OTHER PUBLICATIONS

Smith L.E., Chen C., Wehe D.K., He Z. Hybrid Collimation For Industrial Gamma-Ray Imaging: Combining Spatially Coded And Compton Aperture Data. Nuclear Instruments and Methods in Physics Research Section A: Accelerators, Spectrometers, Detectors and Associated Equipment 462.3 (2001): 578-587.

(Continued)

*Primary Examiner* — Marcus Taningco
(74) *Attorney, Agent, or Firm* — Lathrop & Gage LLP

(57) ABSTRACT

A system for imaging a gamma source includes a pixelated Compton scattering layer, for Compton scattering of gamma photons emitted by the gamma source, and a non-pixelated full-energy detector for detecting at least a portion of Compton scattered gamma photons geometrically encoded by a coded aperture positioned between the pixelated Compton scattering layer and the full-energy detector at a distance from the pixelated Compton scattering layer. A method for imaging a gamma source includes (a) detecting coincidence events, each including Compton scattering in a pixelated Compton scattering layer, and transmission to a non-pixelated full-energy detector of a Compton scattered gamma photon transmitted through a coded aperture located at a distance from the pixelated Compton scattering layer, and (b) determining an image of the gamma source from the detection of the coincidence events.

25 Claims, 22 Drawing Sheets

(56) References Cited

U.S. PATENT DOCUMENTS

| | | | |
|---|---|---|---|
| 8,338,793 B2 | 12/2012 | DeVito | |
| 2002/0008205 A1* | 1/2002 | Kurfess et al. | 250/370.13 |
| 2004/0084624 A1* | 5/2004 | Meng et al. | 250/363.1 |
| 2005/0001213 A1* | 1/2005 | Tindall et al. | 257/52 |
| 2009/0008565 A1* | 1/2009 | Gottesman | 250/370.06 |
| 2009/0122958 A1* | 5/2009 | Mihailescu et al. | 378/87 |

OTHER PUBLICATIONS

Schmid G.J., Beckedahl D.A., Kammeraad J.E., Blair J.J., Vetter K., Kuhn A. Gamma-ray Compton amera imaging with a segmented HPGe. Nuclear Instruments and Methods in Physics Research Section A: Accelerators, Spectrometers, Detectors and Associated Equipment 459.3 (2001): 565-576.

Smith L.E., He Z., Wehe D.K., Knoll G.F., Wilderman S.J. Design and Modeling of the Hybrid Portable Gamma Camera System. Nuclear Science 45.3 (1998): 963-969.

Schultz L.J., Wallace M.S., Galassi M.C., Hoover A.S., Mocko M. Hybrid coded aperture and Compton imaging using an active mask. Nuclear Instruments and Methods in Physics Research Section A: Accelerators, Spectrometers, Detectors and Associated Equipment. 608.2 (2009): 267-274.

Barrett, H. H. and Myers, K., Foundations of Image Science, John Wiley & Sons, Inc., Hoboken, New Jersey, 2004, p. 55.

Canberra, Basic Counting Systems (earliest known availability Jun. 2006), dated Nov. 2010, 13 pages.

Canberra, Gamma and X-Ray Detection (earliest known availability Jun. 2006), dated Oct. 2010, 5 pages.

Niedermayr, T., et al., "Gamma-ray Imaging with a Coaxial HPGe Detector," Nuclear instruments & methods in physics research. Section A, Accelerators, spectrometers,detectors and associated equipment., vol. 553, No. 3, 2005, pp. 501-511.

Rennie, G. "Imagers Provide Eyes to See Gamma Rays" Lawrence Livermore National Laboratory, May 2006, 7 pages.

* cited by examiner

GAMMA RAY IMAGING SYSTEMS AND METHODS

CROSS-REFERENCE TO RELATED APPLICATIONS

The present application claims the benefit of priority to U.S. Provisional Application No. 61/808,881 filed Apr. 5, 2013, which is incorporated herein by reference in its entirety.

BACKGROUND

Gamma ray imaging systems are employed in a variety of fields including nuclear medicine, homeland security, decommissioning of nuclear power plants, and astronomy. Conventional gamma ray imaging systems incorporate pixelated full-energy detectors for measuring the position and energy of gamma photons incident thereupon.

One commonly used system is a Compton camera, which consists of two pixelated detectors, a pixelated Compton scattering layer and a pixelated full-energy detector typically arranged at a distance from each other and parallel to each other. The Compton scattering layer serves to produce scattered gamma photons through Compton scattering of photons from gamma sources. Compton scattering is an inelastic scattering process in which a photon interacts with an electron, to produce a scattered photon. The electron absorbs a portion of the energy of the original photon such that the scattered photon is less energetic than the original photon. This energy difference is denoted the Compton energy shift. In addition, the propagation direction of the scattered photon differs from the propagation direction of the original photon by the Compton scattering angle. Energy and momentum conservation defines a correspondence between the Compton energy shift and the Compton scattering angle. The Compton scattering layer measures the position of a Compton scattering event as well as the associated Compton energy shift. The full-energy detector serves to measure the position and full energy of a scattered photon produced from Compton scattering in the Compton scattering layer. The Compton camera measures the position and Compton energy shift of a Compton scattering event in coincidence with the position and full energy of the scattered photon produced in the Compton scattering event. The locations of the gamma sources producing the original photons, as well as the energies of the gamma photons emitted by the gamma sources, are calculated from a number of coincidence measurements.

Since the Compton detector collects event data in coincidence, it has low background. However, pixelated full-energy detectors are expensive and suffer from low detection efficiency, unless manufactured with very large pixels, which further increases cost.

Another commonly used gamma ray imaging system is a coded aperture camera consisting of a coded aperture and a pixelated full-energy detector. The coded aperture is a substrate with several apertures arranged in a position-dependent pattern. Gamma photons emitted by a gamma source must pass through the coded aperture to reach the pixelated full-energy detector. The coded aperture leaves a position-dependent imprint on the image formed on the pixelated full-energy detector. A true image of the gamma source is reconstructed from the measured image and the known configuration of the coded aperture. The pixelated full-energy detector directly provides the energy spectrum of gamma photons emitted by the gamma source. Since the coded aperture camera does not use coincidence measurements, it may operate at higher detection efficiency than a Compton camera. However, the images tend to have more noise as the system does not use coincidence detection methods to filter out false events.

SUMMARY

In an embodiment, a system for imaging at least one gamma source includes a pixelated Compton scattering layer, for producing scattered gamma photons from Compton scattering of gamma photons emitted by the gamma source, and a non-pixelated full-energy detector for detecting at least a portion of the scattered gamma photons geometrically encoded by a coded aperture, which is located at a distance from the pixelated Compton scattering layer and positioned between the pixelated Compton scattering layer and the full-energy detector.

In an embodiment, a method for imaging at least one gamma source includes (a) detecting a plurality of coincidence events, each coincidence event including Compton scattering of a gamma photon in a pixelated Compton scattering layer, wherein the gamma photon is emitted by the gamma source, and transmission of a scattered gamma photon to a non-pixelated full-energy detector, wherein the scattered gamma photon is produced in the Compton scattering and transmitted through a coded aperture located at a distance from the pixelated Compton scattering layer, and (b) determining an image of the gamma source from the detection of the plurality of coincidence events.

DETAILED DESCRIPTION OF THE EMBODIMENTS

Disclosed herein are gamma ray imaging systems, and associated methods, that determine the position and energy of gamma sources within its field of view without using a pixelated full-energy detector. This provides for a less expensive system than conventional gamma ray imaging systems, such as a conventional Compton camera or a conventional coded aperture camera. The presently disclosed gamma ray imaging system instead incorporates a non-pixelated full-energy detector, which has greater detection efficiency than a pixelated full-energy detector. In addition, the present gamma ray imaging systems utilize coincidence measurements, which reduces the background level compared to systems that do not use coincidence methods to filter detected events.

Figure 1:
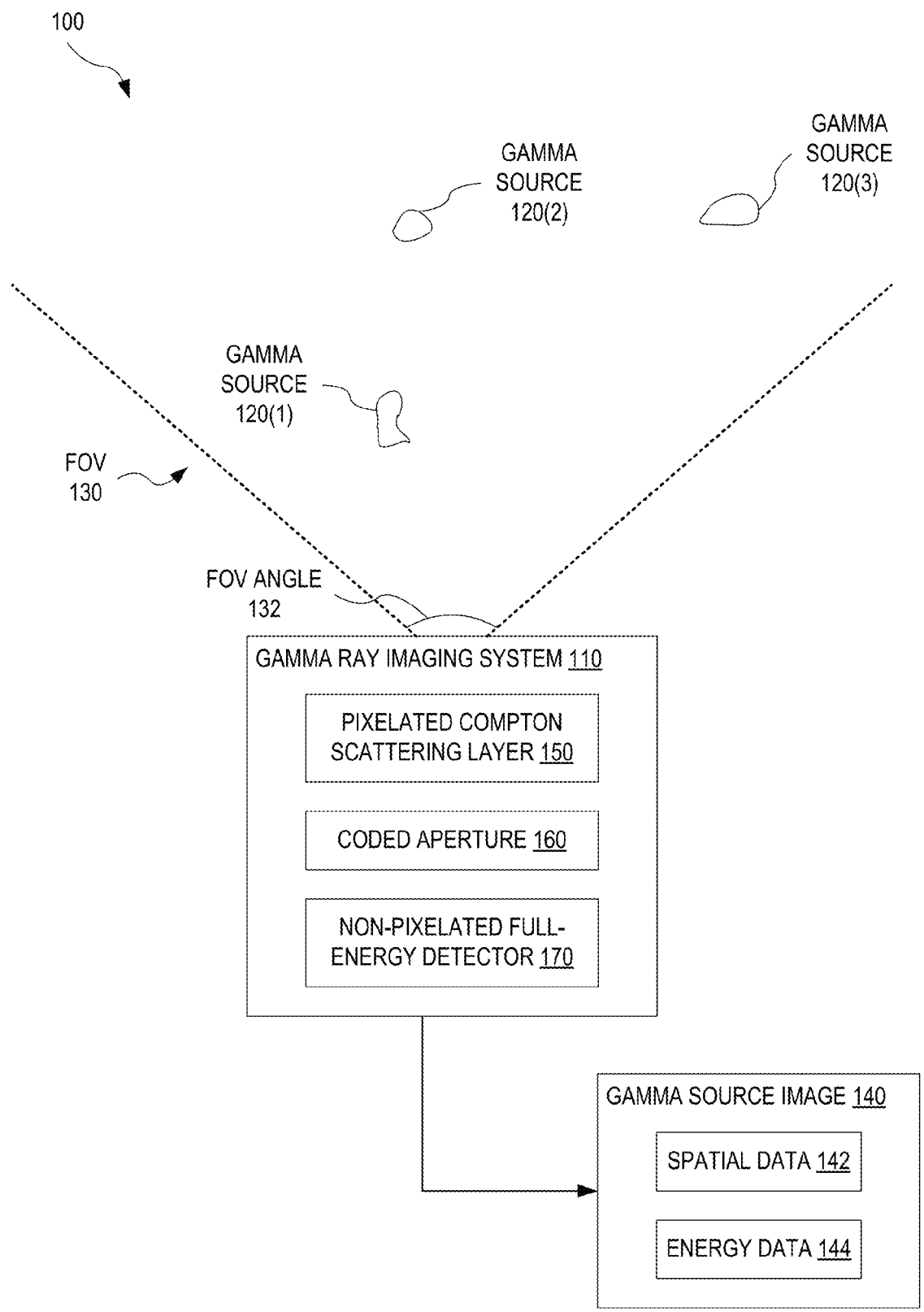
FIG. 1 illustrates a scenario for imaging gamma sources using a gamma ray imaging system that includes a pixelated Compton scattering layer, a coded aperture, and a non-pixelated full-energy detector, according to an embodiment.

FIG. 1 illustrates a scenario 100 for imaging gamma sources using one exemplary gamma ray imaging system 110. Gamma ray imaging system 110 interrogates gamma photons emitted by one or more exemplary gamma sources 120($i$) located within a field of view (FOV) 130 to produce a gamma source image 140. In an embodiment, a FOV angle 132 defines field of view 130. FOV angle 132 is, for example, an angle of 120° or less. Gamma ray imaging system 110 includes a pixelated Compton scattering layer 150, a coded aperture 160, and a non-pixelated full-energy detector 170. Gamma ray imaging system 110 processes measurements from Compton scattering layer 150 and full-energy detector 170 to determine the spatial configuration of gamma sources 120($i$) and/or the energy of gamma photons emitted by gamma sources 120($i$). Accordingly, gamma source image 140 includes spatial data 142 and/or energy data 144. Spatial data 142 is, for example, the location and extent of gamma sources 120($i$). Gamma ray imaging system 110 may be configured to interrogate all of FOV 130, or a portion thereof.

In one embodiment, gamma source image 140 includes a series of images to express spatial data 142 and energy data 144. For example, each image in the series of images includes spatial data 142 for a respective energy range, where the energy range is a subset of energy data 144. In another embodiment, a single image indicates both spatial data 142 and energy 144. For example, a spatial image indicating spatial data 142 is further subdivided such that each spatial location includes associated energy data from energy data 144. In yet another embodiment, gamma ray imaging system 110 provides gamma source image 140 in a tabular or list form, which may subsequently be manipulated to express spatial data 142 and energy data 144 in a desired format.

In an embodiment applicable to near-field operation of gamma ray imaging system 110, where gamma sources 120($i$) are located relatively close to gamma ray imaging system 110, spatial data 142 includes the three-dimensional spatial configuration of gamma sources 120($i$). The three-dimensional spatial configuration is indicated, for example, as the three-dimensional spatial distribution of gamma sources 120($i$) relative to gamma ray imaging system 110. In an embodiment, spatial data 142 includes the spatial configuration of gamma sources 120($i$) in a two-dimensional space defined by angles of the lines of sight from gamma ray imaging system 110 to locations within field of view 130. This embodiment is applicable to far-field operation of gamma ray imaging system 110, where gamma sources 120($i$) are located relatively far from gamma ray imaging system 110.

Figure 2:
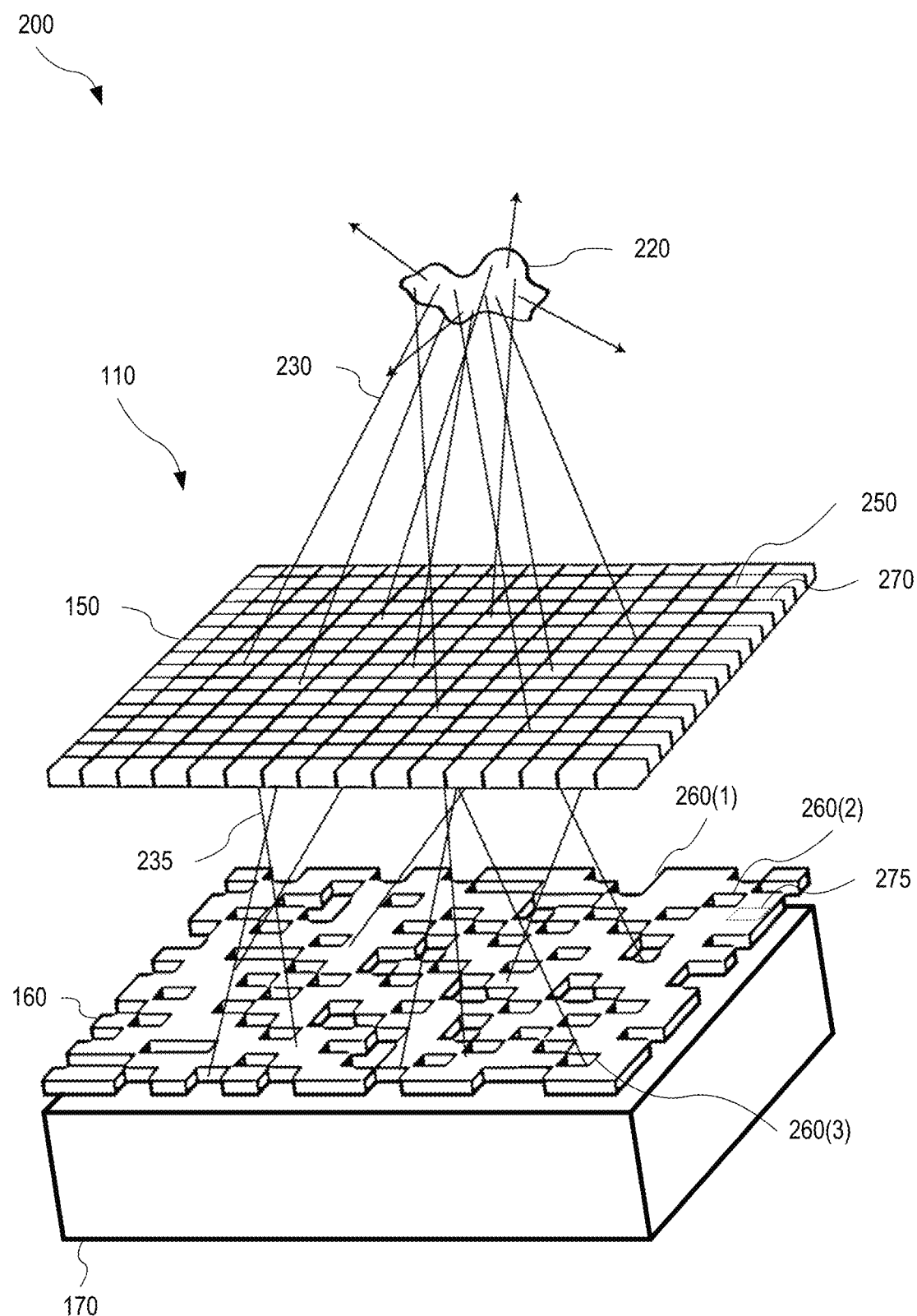
FIG. 2 illustrates a scenario, wherein the gamma ray imaging system of FIG. 1 images an exemplary gamma source, according to an embodiment.

FIG. 2 illustrates a scenario 200, in which gamma ray imaging system 110 images an exemplary gamma source 220. Coded aperture 160 (FIG. 1) is located between Compton scattering layer 150 (FIG. 1) and full-energy detector 170 (FIG. 1), at a distance from Compton scattering layer 150. Full-energy detector 170 (FIG. 1) may be located in immediate contact with coded aperture 160 (FIG. 1) or at a distance therefrom. Pixelated Compton scattering layer 150 includes a plurality of pixels 250 (only one pixel 250 is labeled in FIG. 2). An exemplary gamma photon 230 (only one gamma photon 230 is labeled in FIG. 2) emitted from gamma source 220 in a direction towards a pixel 250 of Compton scattering layer 150 may undergo Compton scattering in pixel 250. Compton scattering may produce a scattered gamma photon 235 (only one scattered gamma photon 235 is labeled in FIG. 2) propagating in a direction towards coded aperture 160. Coded aperture 160 includes a plurality of apertures 260 (three apertures 260(1), 260(2), and 260(3) are labeled in FIG. 2). Apertures 260 are arranged in a position-dependent pattern. If the propagation direction of scattered gamma photon 235 coincides with an aperture 260 of coded aperture 160, scattered gamma photon 235 reaches full-energy detector 170. On the other hand, if the propagation direction of scattered gamma photon 235 does not coincide with an aperture 260 of coded aperture 160, scattered gamma photon 235 is stopped by coded aperture 160.

Although it is anticipated by FIG. 2 that Compton scattering layer 150, coded aperture 160, and full-energy detector 170 are arranged to be parallel to each other, i.e., the surfaces of these elements that face gamma source 220 are parallel, non-parallel geometries may be used without departing from the scope hereof. For example, coded aperture 160 may be arranged at an angle away from being parallel with Compton scattering layer 150 and full-energy detector 170, and/or be a non-planar substrate. Likewise, while FIG. 2 indicates that the surfaces of Compton scattering layer 150, coded aperture 160, and full-energy detector 170, facing gamma source 220, have the same surface area, actual geometries may differ therefrom without departing from the scope of the present disclosure. For example, full-energy detector 170 may have a greater surface area than coded aperture 160 in embodiments where full-energy detector 170 is positioned at a distance form coded aperture 160.

The material and thickness of pixels 250 of Compton scattering layer 150 is such that gamma photons may undergo Compton scattering in pixels 250. Compton scattering is a particularly likely outcome for gamma photons in the mid-energy range from a few kiloelectronvolt (keV) to 1022 keV. At lower energies, the gamma photon may be fully absorbed through the photoelectric effect. At energies 1022 keV, or greater, the gamma photon may instead convert at least a portion of its energy to electron-positron pair production. This type of event has a low probability unless the incident photon energy exceeds 1500 keV.

Figure 3:
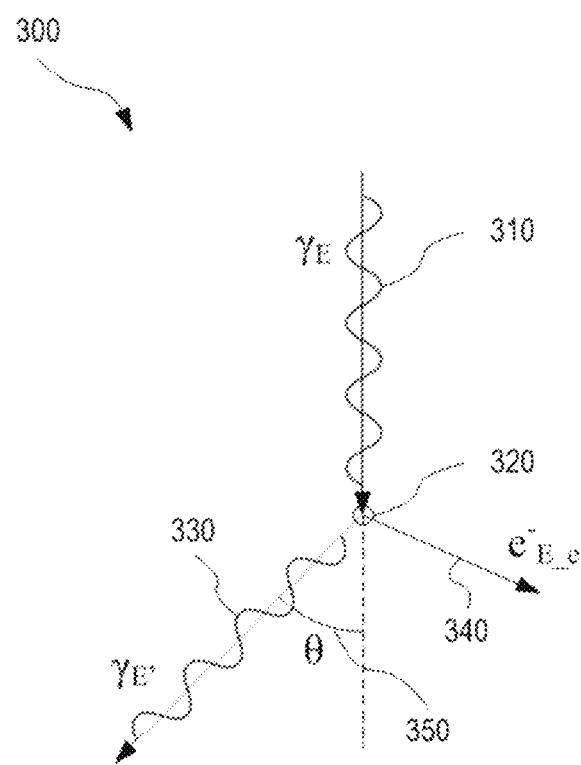
FIG. 3 is a diagram showing the process of Compton scattering in a two-dimensional case.

FIG. 3 is a diagram 300 illustrating the process of Compton scattering. A gamma photon 310 of energy E interacts with an electron 320, or another charged particle, to produce a scattered gamma photon 330 of energy E', where E' is smaller than E. According to the law of energy conservation, electron 320 absorbs the energy E'-E from gamma photon 310. The energy E'-E is known as the Compton energy shift. Electron 320 carries this energy as kinetic energy and moves in a direction indicated by arrow 340, governed by the laws of energy and momentum conservation. Diagram 300 illustrates Compton scattering in the initial, pre-scattering rest frame of electron 320. The laws of energy and momentum conservation define the relationship between energies E and E' and a scattering angle θ (label 350), where the scattering angle θ is the difference in the propagation directions of gamma photon 310 and scattered gamma photon 330:

$$\frac{1}{E'} - \frac{1}{E} = \frac{1}{m_e c^2}(1 - \cos\theta). \quad \text{(Eq. 1)}$$

$m_e$ denotes the mass of electron 320 and c is the speed of light. While diagram 300 shows a two-dimensional case of the Compton scattering process, wherein the propagation directions of gamma photon 310, electron 320, and scattered gamma photon 330 propagate are co-planar, Compton scattering is generally not restricted to two dimensions.

Figure 4:
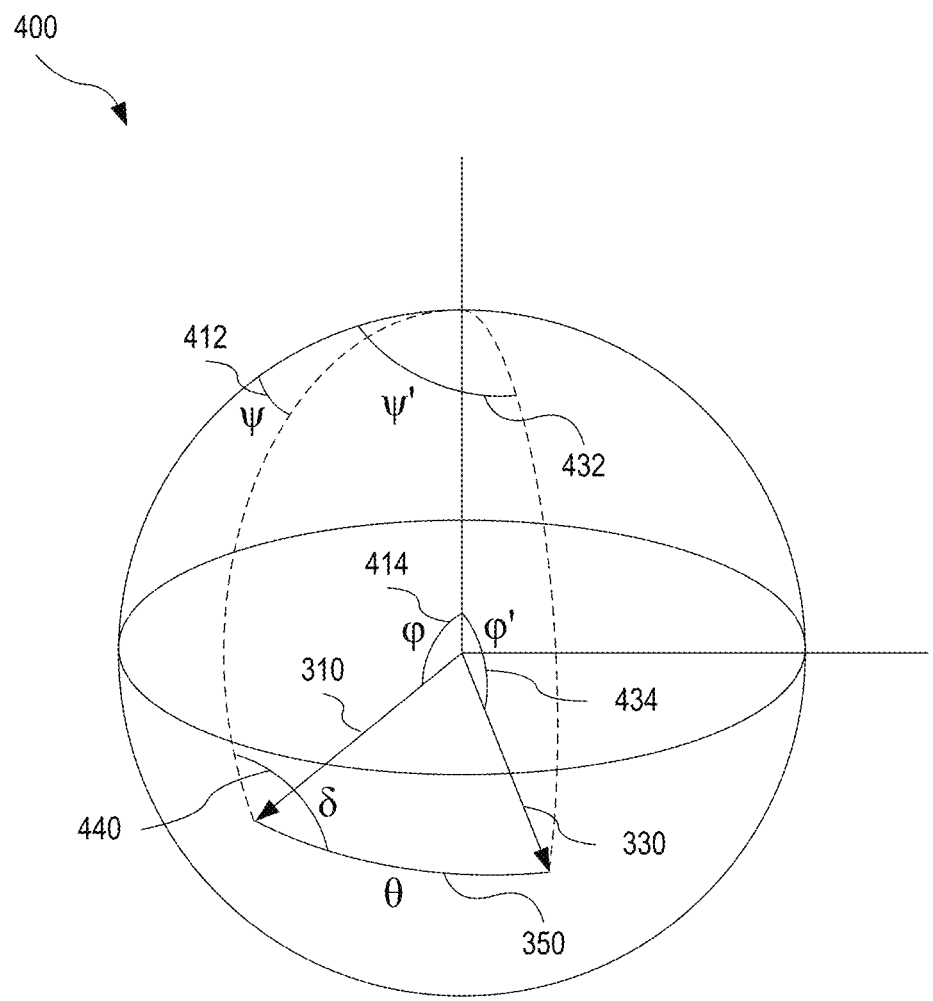
FIG. 4 is a diagram showing the relative propagation directions of a gamma photon and an associated Compton scattered gamma photon in a general, three-dimensional case.

FIG. 4 is a diagram 400 showing the relative propagation directions of gamma photon 310 and scattered gamma photon 330 in the general, three-dimensional case. In this general case, the propagation direction of gamma photon 310 may be expressed by an azimuthal angle ψ (label 412) and a polar angle φ (label 414). Equivalently, the propagation direction of scattered gamma photon 330 may be expressed by an azimuthal angle ψ (label 432) and a polar angle φ' (label 434). Taking the propagation direction of gamma photon 310 as a reference direction, the propagation direction of scattered gamma photon 330 relates thereto through the scattering angle θ (label 350) and a dihedral angle δ (label 440). Dihedral angle δ (label 440) may take on any value with equal probability. Hence, the possible propagation directions of scattered gamma photon 330, for a given scattering angle θ (label 350), describe a cone as dihedral angle spans it full range of possible values.

Returning to FIG. 2, Compton scattering in a pixel 250 of a gamma photon 230 of energy E produces a scattered gamma photon 235 of energy E'. In an embodiment, the material and thickness of Compton scattering layer 150 is such that scattered gamma photon 235 escapes Compton scattering layer 150 without undergoing Compton scattering itself. Compton scattering layer 150 is, for example, a silicon detector with a thickness around 2-3 millimeters. In this case, Compton scattering efficiency for normally incident gamma photons 230 ranges from 6.53% at 150 keV to 2.39% at 1500 keV. For gamma photons 230 incident at an angle of 60° from normal incidence, the Compton scattering efficiency ranges from 12.6% at 150 keV to 4.72% at 1500 keV. At these Compton scattering efficiencies, it is reasonable to assume that an incident gamma photon 230 induces at most one Compton scattering event in Compton scattering layer 150. Hence, scattered gamma photon 235 escapes Compton scattering layer 150.

For a Compton scattering event occurring in a pixel 250, Compton scattering layer 150 (FIGS. 1 and 2) detects both the location of the pixel 250 and the energy absorbed by the electron involved in the Compton scattering event. The measured energy equals the Compton energy shift E-E', where E is the energy of gamma photon 230 and E' is the energy of scattered gamma photon 235.

Figure 5:
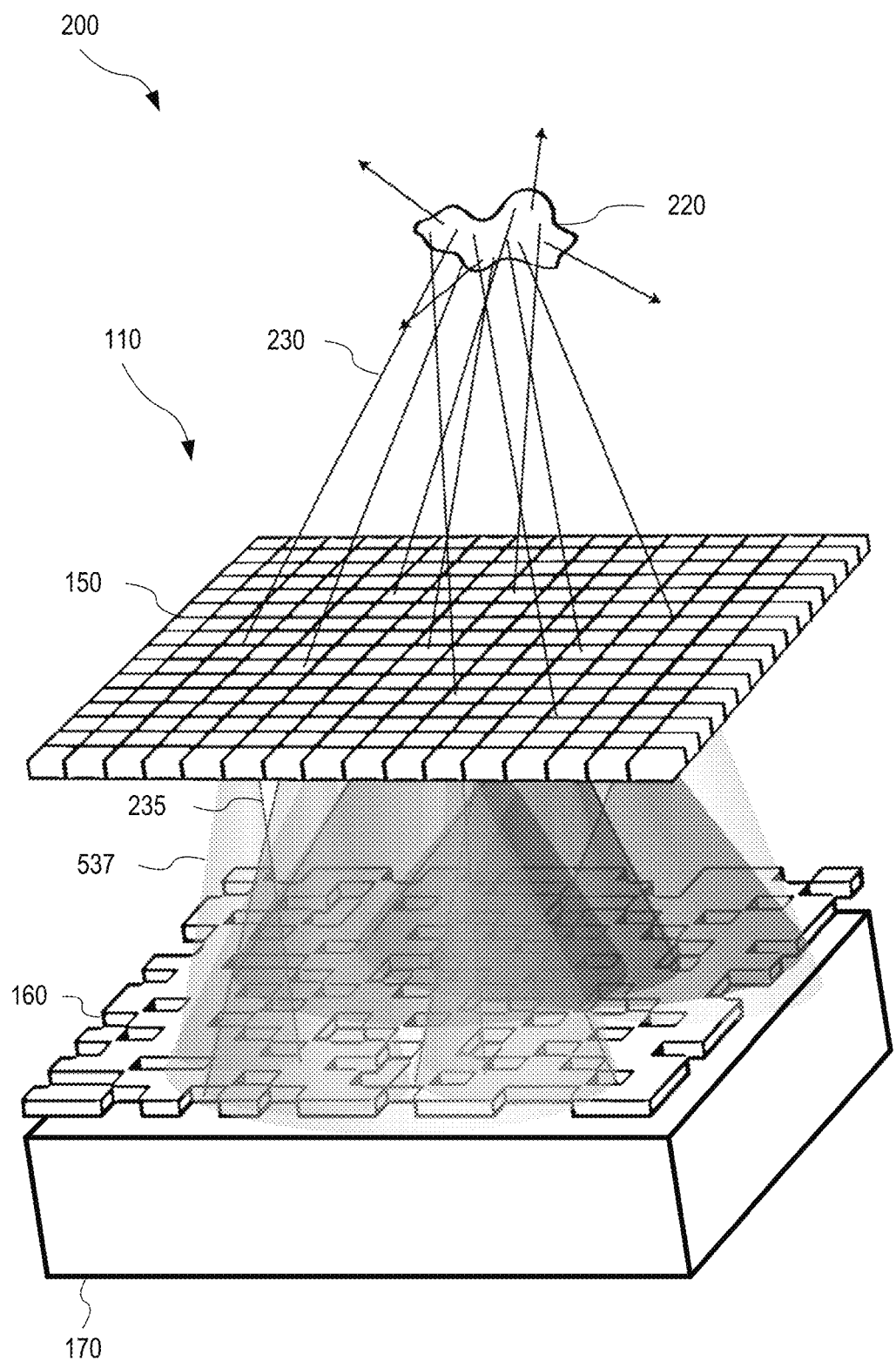
FIG. 5 illustrates the scenario of FIG. 2 with further indication of the possible propagation directions of scattered gamma photons propagating towards the coded aperture, according to an embodiment.

FIG. 5 illustrates scenario 200 of FIG. 2 with further indication of possible propagation directions of scattered gamma photon 235, for an exemplary scattered gamma photon 235 propagating towards coded aperture 160. According to FIG. 4 and the related discussion, scattered gamma photon 235 propagates in a direction that differs from the propagation direction of gamma photon 230 by the scattering angle θ (label 350 in FIG. 4) and the dihedral angle δ (label 440 in FIG. 4), where the dihedral angle δ may take on any value. Therefore, the possible propagation directions of scattered gamma photon 235 define a cone 537 (only one cone 537 is labeled in FIG. 5).

Returning to FIG. 2, a portion of scattered gamma photons 235 propagate in directions that coincide with an aperture 260 of coded aperture 160. This portion of scattered gamma photons 235 reaches full-energy detector 170. The material and thickness of full-energy detector 170 is such that an incident scattered gamma photon 235 deposits its full energy E' in full-energy detector 170. Full-energy detector 170 measures E'.

In certain embodiments, coded aperture 160 is a thin substrate of a high-density material. Coded aperture 160 is, for example, tungsten alloy. In one embodiment, coded aperture 160 blocks all gamma photons that are incident on portions of coded aperture 160 not coinciding with an aperture 260. In another embodiment, the coded aperture 160 blocks a substantial fraction of gamma photons incident on portions of coded aperture 160 not coinciding with an aperture 260. In an embodiment, the thickness of coded aperture 160, relative to other the dimensions of gamma ray imaging system 110, is such that coded aperture 160 does not act as a collimator. In this case, several physical dimensions of gamma ray imaging system 110 are matched to ensure that a gamma photon entering an aperture 260 of coded aperture 160 has a high probability of passing all the way through aperture 260 to reach full-energy detector 170. The physical dimensions include (a) the distance between Compton scattering layer 150 and coded aperture, (b) the sizes of Compton scattering layer 150 and coded aperture 160 in the transverse dimensions, i.e., the dimensions parallel to the surface of coded aperture 610 facing Compton scattering layer 150, and (c) the thickness of coded aperture 160.

In certain embodiments, coded aperture 160 is based on a rectangular lattice of the same dimensions as pixelated Compton scattering layer 150. Each pixel of Compton scattering layer corresponds to a cell of coded aperture 160. This is illustrated by an exemplary corresponding pair consisting of pixel 270 of Compton scattering layer 150 and cell 275 of coded aperture 160. In general, cells 275 are either open or closed. Single open cells 275 or groups of open cells 275 form apertures 260. The common rectangular lattice of coded aperture 160 and Compton scattering layer 150 ensures that ray pencils formed between the pixels Compton scattering layer 150 and the lattice cells of coded aperture 160 are analogous to the principal lattice directions of a rectangular crystal. Thus, the same scattered photon directions are repeatedly sampled by different paths through the system. In an embodiment hereof, 50% of the lattice cells of coded aperture 160 are open, i.e., form or contribute to apertures 260. This value is a trade-off between maximizing the count rate on full energy detector 170 and minimizing the ambiguity about the path taken by scattered gamma photons 235 through coded aperture 160.

The properties of full-energy detector 170 may be optimized for full-energy measurement of incident scattered gamma photons 235 in a desired energy range. Full-energy detector 170 is a non-pixelated detector, the output of which does not include information about the position of a detection event therein. In an embodiment, full-energy detector 170 is a monolithic, non-pixelated full-energy detector such as a scintillator. Since the associated readout circuitry does not need to manage the logistics of multiple pixels, full-energy detector 170 has less dead time than a pixelated full-energy detector such as those used in conventional Compton cameras. The performance of pixelated full-energy detectors typically also suffers from complications caused by gamma photons entering one pixel of the pixelated full-energy detector but penetrating into a neighboring pixel thereof before depositing its full energy. This issue does not apply to the present non-pixelated full energy detector 170.

In an embodiment, full-energy detector 170 is a single semiconductor crystal. Full-energy detector 170 is, for example, a High-Purity Germanium crystal (HPGe). The atomic number of Germanium is higher than that of Silicon and therefore has a greater likelihood of capturing the full energy of scattered gamma photons 235. In an embodiment, full-energy detector 170 is a cooled single semiconductor crystal, for example, HPGe cooled with liquid nitrogen. The cooling serves to reduce electronic noise attributed to thermal electrons bridging the band gap of the semiconductor to create a false signal. In certain embodiments, high-voltage is applied to full-energy detector 170 to increase its sensitivity for detection of single gamma photons. For example, with high-voltage applied to a cooled HPGe crystal, single scattered gamma photons 235 may be detected. The readout circuitry may be optimized to yield a short dead time associated with each event. This allows for detection of single gamma photons at a high rate, which results in high detection efficiency in high count-rate situations. For example, the duration of an electronic readout signal from full-energy detector 170 may be minimized using methods known in the art.

Figure 6:
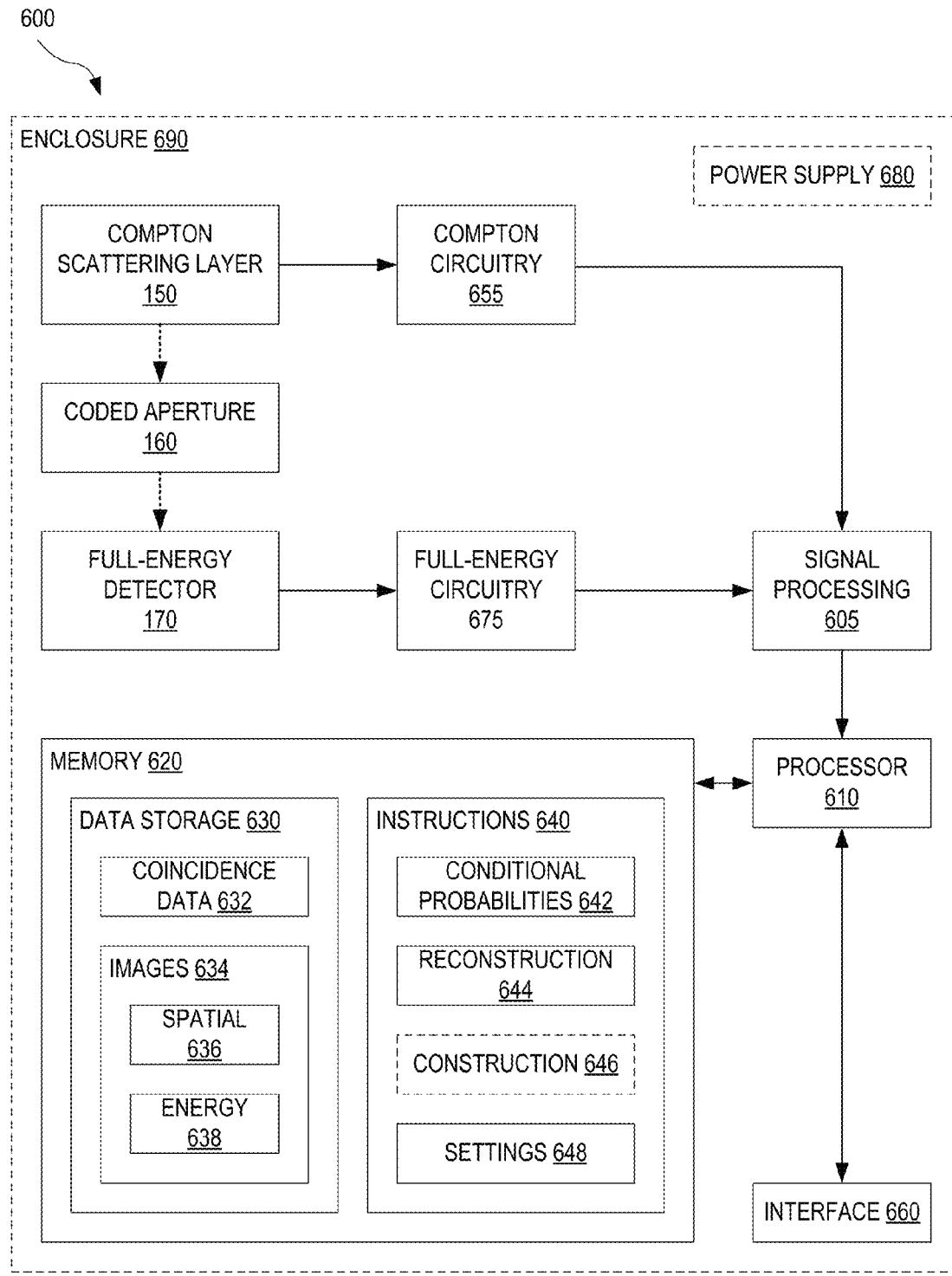
FIG. 6 illustrates a gamma ray imaging system, which is an embodiment of the gamma ray imaging system of FIG. 1.

FIG. 6 illustrates one exemplary gamma ray imaging system 600. Gamma ray imaging system is an embodiment of gamma ray imaging system 110 (FIG. 1). Gamma ray imaging system 600 includes Compton scattering layer 150 (FIGS. 1 and 2), coded aperture 160 (FIGS. 1 and 2), and full-energy detector 170 (FIGS. 1 and 2). Gamma ray imaging system 600 includes Compton electronic circuitry 655 for generating an electronic signal associated with a Compton scattering event in Compton scattering layer 150, for example scattering of gamma photon 230 (FIG. 2) to produce scattered gamma photon 235 (FIG. 2). The electronic signal indicates the Compton energy shift $E'-E$ of the Compton scattering event, for example through a pulse height, and the location of the Compton scattering event, i.e., the pixel in which the event occurred. Similarly, Gamma ray imaging system 600 includes full-energy electronic circuitry 675 for generating an electronic signal associated with the detection of a gamma photon in full-energy detector 170, for example scattered gamma photon 235 (FIG. 2). Full-energy electronic circuitry 675 indicates the energy deposited in full-energy detector 170 by a gamma photon, for example through a pulse height. A signal processing unit 605 processes the electronic signals, generated by Compton electronic circuitry 655 and full-energy circuitry 675.

Gamma ray imaging system 600 further includes a processor 610, a memory 620, and an interface 660. Memory 620 includes a data storage 630 and machine-readable instructions 640 encoded in non-volatile memory. Processor 610 is communicatively coupled with signal processing unit 605 for receiving, for example, coincidence data generated by signal processing unit 605. Processor 610 is also communicatively coupled with memory 620 for accessing data storage 630 and instructions 640. Processor 610 is communicatively couple to interface 660 for outputting data. Processor 610 may further receive instructions from interface 660. Such instructions may include settings for signal processing performed by signal processing unit 605, additional settings required to for processor 610 to execute certain portions of instructions 640, or changes to instructions 640. Interface 660 may include a display and one or more wired or wireless communications ports.

Signal processing unit 605, processor 610, and memory 620 together form a data processing system that processes the outputs of Compton electronic circuitry 655 and full-energy circuitry 675 to determine an image of one or more gamma sources within a field of view of gamma ray imaging system 600.

Data storage 630 includes coincidence data 632 for storage of coincidence data generated by signal processing unit 605 and received from processor 610. Data storage 630 further includes an image storage 634 for storage of images, such as gamma source image 140 (FIG. 1) of at least a portion of a field of view gamma ray imaging system 600. Image storage 634 includes spatial data 636 and energy data 638, as discussed in connection with FIG. 1. Instructions 640 include conditional probabilities 642, reconstruction instructions 644, settings 648, and optionally construction instructions 646, all of which are discussed below. Instructions 640 and processor 610 together form a data analysis module for determining an image of one or more gamma sources within a field of view of gamma ray imaging system 600 from coincidence data 632.

Optionally, gamma ray imaging system 600 includes a power supply 680, for example a battery. Gamma ray imaging system 600 may further include an enclosure 690 for environmental protection or shielding of components.

Figure 7:
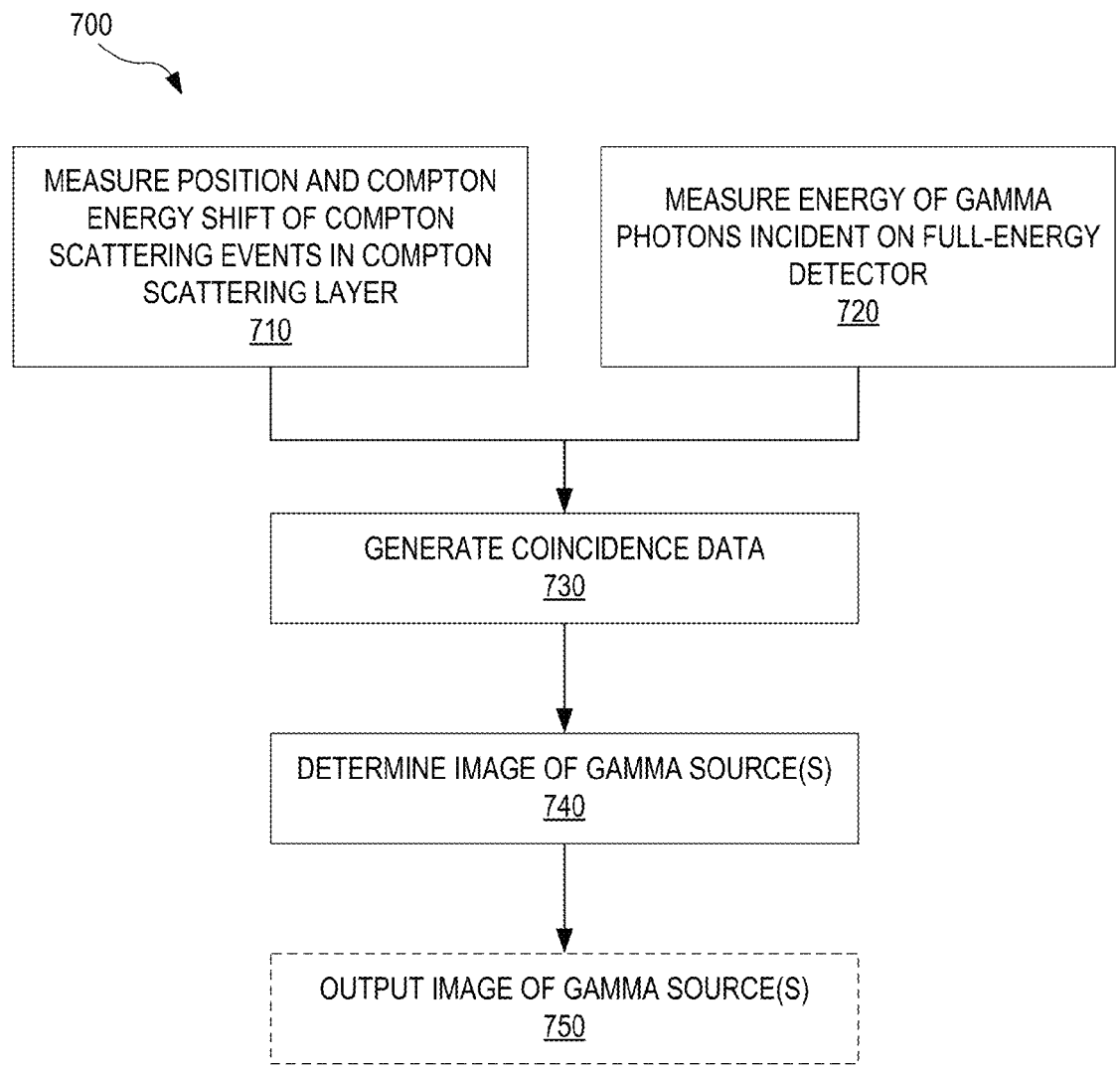
FIG. 7 illustrates a method for determining an image of gamma sources within at least a portion of a field of view of that gamma ray imaging system of FIG. 1, according to an embodiment.

FIG. 7 illustrates one exemplary method 700 for determining an image of gamma sources within at least a portion of a field of view of a gamma ray imaging system 110 (FIGS. 1 and 2). Method 700 may be performed by gamma ray imaging systems 110 (FIGS. 1 and 2) or 600 (FIG. 6). In a step 710, the position and Compton energy shift, of a Compton scattering event in Compton scattering layer 150 (FIGS. 1 and 2), is measured. For example, gamma ray imaging system 600 (FIG. 6) measures the position and Compton energy shift of a Compton scattering event in Compton scattering layer 150 (FIGS. 1, 2, and 6) using Compton electronic circuitry 655 (FIG. 6). In a step 720, the energy of gamma photons incident on full-energy detector 170 (FIGS. 1 and 2) is measured. For example, gamma ray imaging system 600 (FIG. 6) measures the energy of a gamma photon in full-energy detector 170 (FIGS. 1, 2, and 6) using full-energy electronic circuitry 675 (FIG. 6).

In a step 730, data generated in steps 710 and 720 is processed to generate coincidence data. Coincidence data is data composed of measurements obtained from Compton scattering layer 150 (FIGS. 1 and 2) in step 710 and full-energy detector 170 (FIGS. 1 and 2) in step 720, for near-simultaneous events in Compton scattering layer 150 (FIGS. 1 and 2) and full-energy detector 170 (FIGS. 1 and 2), where "near-simultaneous" is defined by an appropriate upper limit on the time between detection of events in Compton scattering layer 150 (FIGS. 1 and 2) and full-energy detector 170 (FIGS. 1 and 2). With appropriate time difference criteria, the coincidence data includes only data for events, wherein a gamma photon undergoes Compton scattering in Compton scattering layer 150 (FIGS. 1 and 2) to produce a scattered gamma photon that is transmitted by coded aperture 160 (FIGS. 1 and 2) to be detected by full-energy detector 170 (FIGS. 1 and 2). An insignificant number of false coincidences, where unassociated events occurred nearly simultaneously in Compton scattering layer 150 and full-energy detector 170, may be included in the coincidence data. However, a large amount of background is eliminated by invoking the coincidence requirement. Step 730 is, for example, performed by signal processing unit 605 (FIG. 6) by processing electronic signals received from Compton electronic circuitry 655 (FIG. 6) and full-energy electronic circuitry 675 (FIG. 6). In an embodiment, signal processing unit 605 (FIG. 6) is preconfigured with time difference criteria. In another embodiment, signal processing unit 605 (FIG. 6) receives time difference criteria from processor 610 (FIG. 6). Processor 610 (FIG. 6) obtains these time difference criteria from instructions 640 (FIG. 6) or from interface 660 (FIG. 6).

In a step 740, the coincidence data generated in step 730 are processed to determine an image of gamma sources within the field of view, or portion thereof, of gamma ray imaging system 110 (FIGS. 1 and 2). Since the image is determined from coincidence data, it has a lower background level than images determined without requiring coincidence. Particular embodiments of step 740 are discussed below.

A conceptual understanding of how an image may be determined in step 740 may be obtained by considering the information provided by the coincidence data generated in step 730. The coincidence data includes, for each coincidence event, the position of the Compton scattering event in Compton scattering layer 150, the Compton energy shift E−E', and the energy E' of the scattered gamma photon. From this information, the energy of the gamma photon, emitted by gamma source, may be determined, and the scattering angle θ may then be determined using Eq. 1. However, since full-energy detector 170 is not pixelated, the position at which the scattered gamma photon deposits its energy in full-energy detector 170 is not known for a given coincidence event. Coded aperture 160 compensates for this, as its presence encodes additional geometrical information into the energy measurements obtained from full-energy detector 170. Consider coincidence events associated with a given pixel 250 of Compton scattering layer 150. Since not all propagation angles from Compton scattering layer 150 to full-energy detector 170 are possible, the corresponding energy spectrum of scattered gamma photons, measured by full-energy detector 150, is encoded with the pattern of apertures 260 of coded aperture 160. Consequently, the coincidence data obtained in step 730 has encoded therein additional information relating to the position at which scattered gamma photons deposit their energy in full-energy detector 170.

Although all required information is included in the coincidence data obtained in step 730, it is not possible to determine the propagation angle between Compton scattering layer 150 and full-energy detector 170 for each individual coincidence event. It is also not possible to determine the image using a simple deconvolution method. In certain embodiments, step 740 determines the image as the statistically most likely image based on the coincidence events generated in step 730.

In an optional step 750, the image obtained in step 740 is outputted. For example, processor 610 (FIG. 6) stores the image to images 634 (FIG. 6) and/or sends the image to interface 660 (FIG. 6). The image includes spatial data 636 (FIG. 6) that specify the location of gamma sources within the field of view of gamma ray imaging system 110 (FIG. 1). In one embodiment, spatial data 636 specify the location of gamma sources in three dimensions. In another embodiment, spatial data 636 gamma sources are located in two dimensions, for example, expressed in terms of a viewing angle from gamma ray imaging system 110 (FIG. 1) to the gamma source. The image further includes energy data 638 (FIG. 6) that specify the energies of gamma photons emitted by the gamma sources. These energies may be used to determine the gamma source material.

Figure 8:
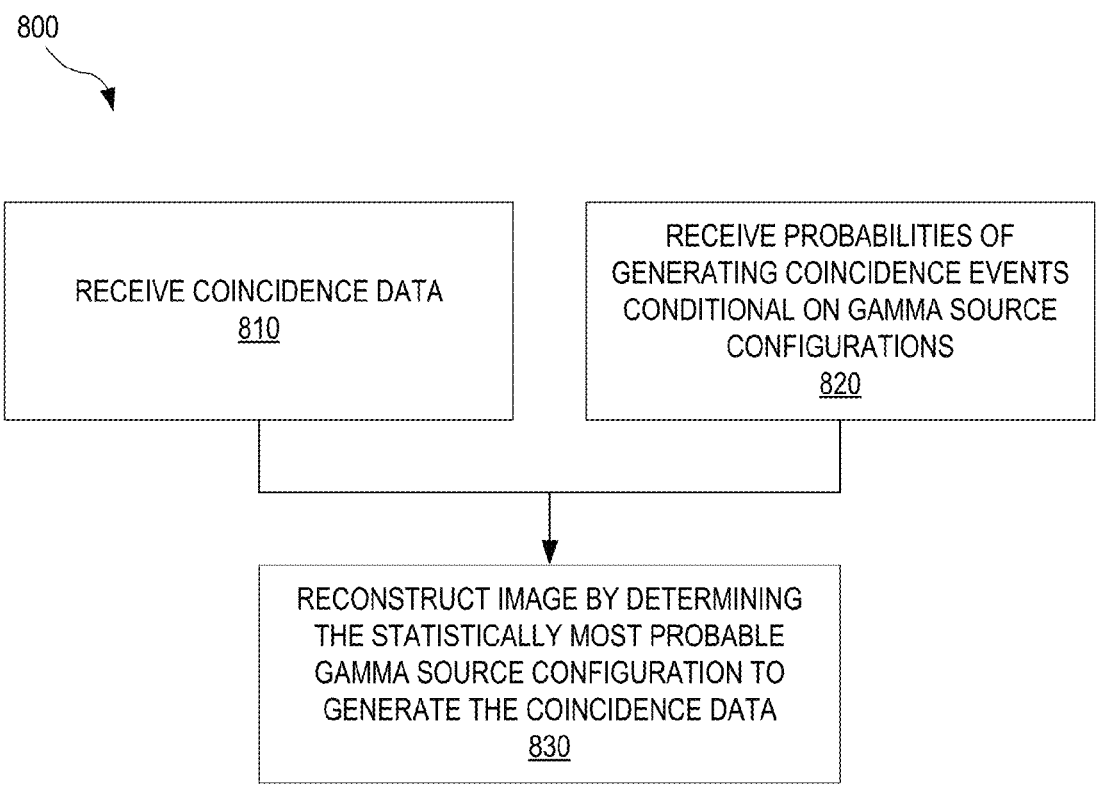
FIG. 8 illustrates a method for processing data acquired by the gamma ray imaging system of FIG. 1 to determine an image of gamma sources within at least a portion of a field of view of the gamma ray imaging system, according to an embodiment.

FIG. 8 illustrates one exemplary method 800 for processing data acquired by gamma ray imaging system 110 (FIGS. 1 and 2) to determine an image of gamma sources within at least a portion of a field of view of gamma ray imaging system 110 (FIGS. 1 and 2). Method 800 is an embodiment of step 740 of method 700 (FIG. 7). In a step 810, coincidence data is received. For example, processor 610 (FIG. 6) receives coincidence data from signal processing unit 605 (FIG. 6) and stores the coincidence data to coincidence data 632 (FIG. 6). Processor 610 (FIG. 6) may receive and store coincidence data on an ongoing basis as it is generated by signal processing unit 605 (FIG. 6). When a sufficient amount of coincidence data has been accumulated, processor 610 (FIG. 6) may retrieve the coincidence data from coincidence data 632 (FIG. 6).

In a step 820, probabilities of generating all possible types of coincidence events, conditional on all possible gamma source configurations within the field of view or portion thereof, are received. The conditional probabilities are associated with certain resolutions of both the object space and the measurement space. The object space is a desired portion of the field of view of gamma ray imaging system 110 (FIG. 1), i.e., a space viewed by gamma ray imaging system 110 (FIG. 1) and considered in the analysis of measurements performed by gamma ray imaging system 110 (FIG. 1). Processor 610 (FIG. 6), for example, performs step 820. Processor 610 (FIG. 6) may receive the conditional probabilities from conditional probabilities 642 (FIG. 6) or from interface 660 (FIG. 6). The object space definition (location and extent), object space resolutions, and measurement space resolutions, may be stored in settings 648 (FIG. 6).

In a step 830, an image of the gamma sources is reconstructed using the coincidence data received in step 810 and the conditional probabilities received in step 820. The image is determined as the statistically most probable gamma source configuration to generate the coincidence data received in step 810. Step 830 is performed, for example, by processor 610 (FIG. 6). Processor 610 (FIG. 6) processes the coincidence events and conditional probabilities according to reconstruction instructions 644 (FIG. 6). This may further include processor 610 retrieving parameters from settings 648 (FIG. 6).

Figure 9:
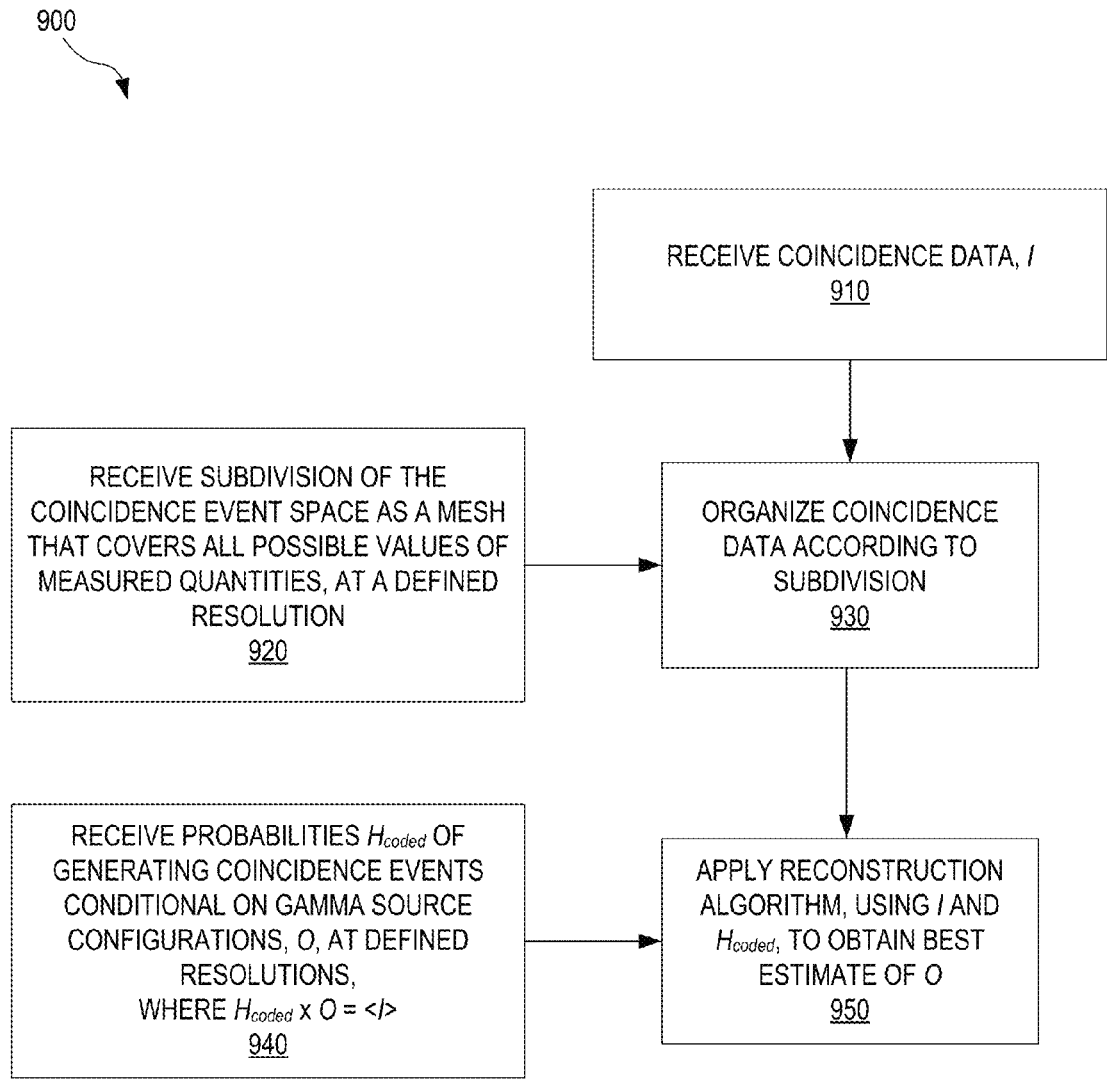
FIG. 9 illustrates a method for reconstructing an image of gamma sources within at least a portion of a field of view of the gamma ray imaging system of FIG. 1, where the image is reconstructed as the statistically most probable image, according to an embodiment.

FIG. 9 illustrates one exemplary method 900 for reconstructing an image of gamma sources within at least a portion of a field of view of gamma ray imaging system 110 (FIG. 1). Method 900 utilizes coincidence data and calculated probabilities of generating all possible types of coincidence events conditional on all possible gamma source configurations within the field of view, or portion thereof. Method 900 is an embodiment of step 830 of method 800 (FIG. 8) and may implemented in gamma ray imaging system 600 (FIG. 6) as reconstruction instructions 644 (FIG. 6).

In a step 910, coincidence data, I, are received. Step 910 is identical to step 810 (FIG. 8). In a step 920, a subdivision of the coincidence event space is received. This subdivision divides the space of possible coincidence events into a mesh that covers all possible values of the measured quantities: location and Compton energy shift of a Compton scattering event in Compton scattering layer 150 (FIG. 1), and energy of the corresponding scattered gamma photon as measured by full-energy detector 170 (FIG. 1). Each entry in the mesh is associated with a single, possible combination of the measured quantities. The mesh has certain resolutions for each of the measured quantities. Step 920 is performed, for example, by processor 610 (FIG. 6). Processor 610 (FIG. 6) retrieves the subdivision from settings 648 (FIG. 6). In a step 930, the coincidence data received in step 910 is organized according to the subdivision received in step 920. In certain embodiments, the coincidence events are arranged in a coincidence event vector, where each entry indicates the number of coincidence events that fell into a particular mesh entry of the subdivision. Step 930 is, for example, performed by processor 610 (FIG. 6) according to instructions 640.

In a step 940, conditional probabilities $H_{coded}$ are received. The conditional probabilities $H_{coded}$ are the probabilities of generating all possible types of coincidence events, conditional on all possible gamma source configurations within the field of view, or portion thereof. $H_{coded}$ has been generated based on (a) specified resolutions of the coincidence event space, as discussed in connection with step 930, and (b) specified resolutions, location and extent of the object space, where the object space includes both spatial dimensions and an energy dimension. $H_{coded}$ is defined as $$H_{coded} = [p(I_i | O_j)], \quad (Eq.\ 2)$$

where $I_i$ is the i'th mesh entry in the subdivision, received in step 920, and $O_j$ is a certain gamma source configuration. In one embodiment, the object space spatial dimensions include three dimensions to define locations of gamma sources, within the field of view, in three dimensions. The three dimensions are three orthogonal dimensions specified, for example, in a Cartesian coordinate system, a spherical coordinate system, or a cylindrical coordinate system. In another embodiment, the object space spatial dimensions include two dimensions to define locations of gamma sources, within the field of view, in two dimensions. The two dimensions are, for example, a viewing direction from gamma ray imaging system 110 (FIG. 1) specified by two orthogonal angles.

In certain embodiments, $I_i$ and $O_j$ are entries in respective vectors I and O, where I is the coincidence vector discussed in connection with step 930, and O is an object vector consisting of all possible locations and energies in the object space. Each entry in O corresponds to a given spatial location and a given gamma photon energy. The object vector O may specify any gamma source configuration by appropriate population of its entries. In such embodiments, $H_{coded}$ is expressed as a matrix that fulfills the equation $$\langle I \rangle = H_{coded} \times O \quad (Eq.\ 3)$$

where $\langle I \rangle$ is the expectation value of the coincidence vector I. Each column of $H_{coded}$ is a vector of the probabilities of a certain set of coincidence events conditional on a certain location and energy in the object space. Each row of $H_{coded}$ is a vector proportional to the likelihood of a certain object location and energy. Step 940 is, for example, performed by processor 610 (FIG. 6). Processor 610 (FIG. 6) retrieves the conditional properties $H_{coded}$ from conditional probabilities 642 (FIG. 6).

In a step 950, a reconstruction algorithm is applied to obtain the best estimate of the object vector O, based upon the coincidence data I organized in step 930 and the conditional probabilities $H_{coded}$ received in step 940. This step is equivalent to substituting the coincidence data I for the expectation value thereof $\langle I \rangle$ in Eq. 3 and solving the modified equation. In certain embodiments, this is done by manipulation of vectors and matrices. In embodiments where the object space is defined in three dimensions, the reconstructed image includes three spatial dimensions to define the location and extent of gamma sources in three dimensions. In embodiments where the object space is defined in two dimensions, the reconstructed image includes two spatial dimensions to define the location and extent of gamma sources in two dimensions. For example, the location and extent of gamma sources, within the field of view or portion thereof, are defined in terms of the viewing angle from gamma ray imaging system 110 (FIG. 1). The viewing angle may be specified by two orthogonal angles. Step 950 is, for example, performed by processor 610 (FIG. 6) according to reconstruction instructions 644 (FIG. 6).

Several statistical methods exist for performing step 950, for example least-squares optimization (LS), maximum-likelihood expectation-maximization (MLEM), cross-correlation, and maximum-entropy. Using the LS method, the best estimate $\langle O \rangle$ of the object vector O may be found as $$\langle O \rangle = (H'_{coded} \times H_{coded})^{-1} H'_{coded} \times I, \quad (Eq.\ 4)$$

where $H'_{coded}$ is the conjugate transpose of $H_{coded}$.

The MLEM method may be performed using a variety of algorithms, each utilizing alternating expectation and maximization steps. MLEM requires the implementation of an iterative method, such as an iteration described by the equation $$f^{k+1} = \frac{f^k}{S}\left(\frac{I}{H_{coded} \times f^k}\right)' H_{coded}. \qquad \text{(Eq. 5)}$$

$f^k$ is the k'th iteration of the reconstructed image, i.e., the k'th iteration of the estimate of the object vector O. S is a sensitivity factor that normalizes the data. S is the column sum of $H_{coded}$. The MLEM method is a multiplicative algorithm that involves multiplying the previous estimate by a correction factor, as opposed to adding it. The term $f^k/S$ of Eq. 4 is merely the previous iteration, scaled. The term $I/(H_{coded} \times f^k)$ is the multiplicative correction factor. The goal is to reach, through iteration, a value of $H_{coded} \times f^k$ that is equal to I. When the next iteration equals the previous, the iteration has converged and the goal is reached. However, if $H_{coded} \times f^k$ is not equal to I, the multiplicative correction factor is a vector of length equal to I, where each element is the ratio of the element in I to the element found when $H_{coded} \times f^k$ is calculated. This provides the appropriate scaling factor to adjust the next step in the algorithm.

A benefit to the MLEM method is that it is based upon an underlying Poisson distribution rather than a Gaussian distribution. This enforces positivity, as long as the given initial estimate, as well as all elements in I and H coded, are also positive. This is particularly beneficial in low-count situations where many entries of the coincidence vector I are zero or near zero. In addition, it may be seen how the iteration converges, since as $H_{coded} \times f^k$ approaches I, the multiplicative factor $I/(H_{coded} \times f^k)$ approaches unity. In the case where $H_{coded} \times f^k$ cannot be exactly equal to I, the method minimizes the Kullback-Leibler distance between the data and the image of the estimate.

The MLEM method is derived from the Poisson likelihood, and therefore, if the iteration converges, it finds the maximum of the log-likelihood. However, if there is noise present, this results in the method forcing agreement with noisy data, and will result in a few very bright entries in the reconstructed image. In an embodiment, the iteration is stopped after a fixed number of iterations in order to avoid amplification of data noise.

Without departing from the scope hereof, method 900 may be performed using a list-mode likelihood method, in which coincidence events are not organized according to a predefined subdivision but rather treated individually as single events.

Figure 10:
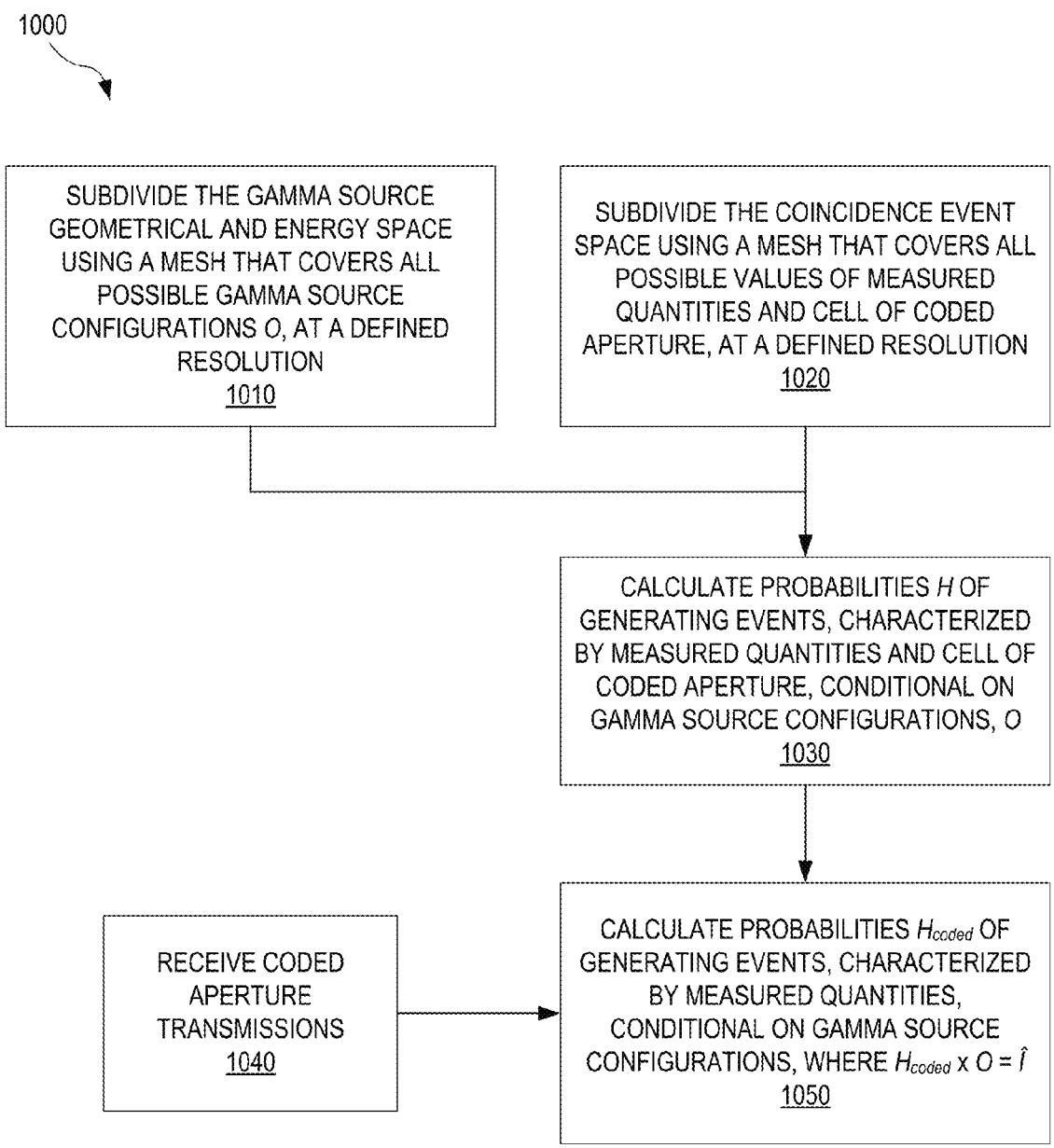
FIG. 10 illustrates a method for calculating conditional probabilities used in the method of FIG. 9, according to an embodiment.

FIG. 10 illustrates one exemplary method 1000 for calculating probabilities of generating all possible types of coincidence events conditional on all possible gamma source configurations within at least a portion of a field of view of gamma ray imaging system 110 (FIG. 1). Method 1000 may be implemented in gamma ray imaging system 600 (FIG. 6) as construction instructions 646 (FIG. 6). Alternatively, method 1000 is performed externally to gamma ray imaging system 600 (FIG. 6) and communicated to processor 610 (FIG. 6) through interface 660 (FIG. 6). Processor 610 (FIG. 6) may then store the conditional probabilities to conditional probabilities 642 (FIG. 6).

In a step 1010, the object space, discussed in connection with step 940 (FIG. 9), is subdivided into an object space mesh that covers all possible spatial locations and energies in the object space. The object space mesh has specified resolutions in each of the spatial dimensions and in the energy dimension. The object space thus subdivided has a certain spatial extent corresponding to a desired portion of the field of view of the gamma ray imaging system. Each entry in the object space mesh defines a single combination of spatial location and energy. Step 1010 is, for example, executed by processor 610 (FIG. 6) according to construction instructions 646 (FIG. 6) and settings 648 (FIG. 6).

In a step 1020, the coincidence event space is subdivided into a coincidence event mesh that covers all possible values of location of cell 275 (FIG. 2) of coded aperture 160 (FIGS. 1 and 2) and the measured quantities. The measured quantities are location and Compton energy shift of a Compton scattering event in Compton scattering layer 150 (FIG. 1), and energy of the corresponding scattered gamma photon as measured by full-energy detector 170 (FIG. 1). Each entry in the coincidence event mesh is associated with a single, possible combination of the measured quantities and the location of cell 275 (FIG. 2). The coincidence event mesh has certain resolutions for each of these quantities. Step 1020 is, for example, executed by processor 610 (FIG. 6) according to construction instructions 646 (FIG. 6) and settings 648 (FIG. 6).

In a step 1030, the probabilities H of generating all possible combinations of measured quantities and the location of cell 275 (FIG. 2) of coded aperture 160 (FIGS. 1 and 2), conditional on all object space locations and energies, are calculated. The calculation is performed using the subdivisions generated in steps 1010 and 1020. The probabilities H are conceptually equivalent to the probabilities $H_{coded}$ discussed in connection with FIG. 9, except that the location of cell 275 (FIG. 2) of coded aperture 160 (FIGS. 1 and 2) is retained in H. Processor 610 (FIG. 6), for example, executes step 1030 according to construction instructions 646 (FIG. 6).

In a step 1040, the transmission values for all cells 275 (FIG. 2) of coded aperture 160 (FIGS. 1 and 2) are received. For example, processor 610 (FIG. 6) receives the transmission values from instructions 640 (FIG. 6) or interface 660 (FIG. 6). In a step 1050, the probabilities H generated in step 1030 are manipulated, according to the transmission values received in step 1040, to generate the probabilities $H_{coded}$ discussed in connection with FIG. 9. In an embodiment, the transmission values are arranged in a matrix T, where $H_{coded}$ may be calculated as $H_{coded} = T \times H$. Step 1050 is, for example, executed by processor 610 (FIG. 6) according to construction instructions 646 (FIG. 6).

Figure 11:
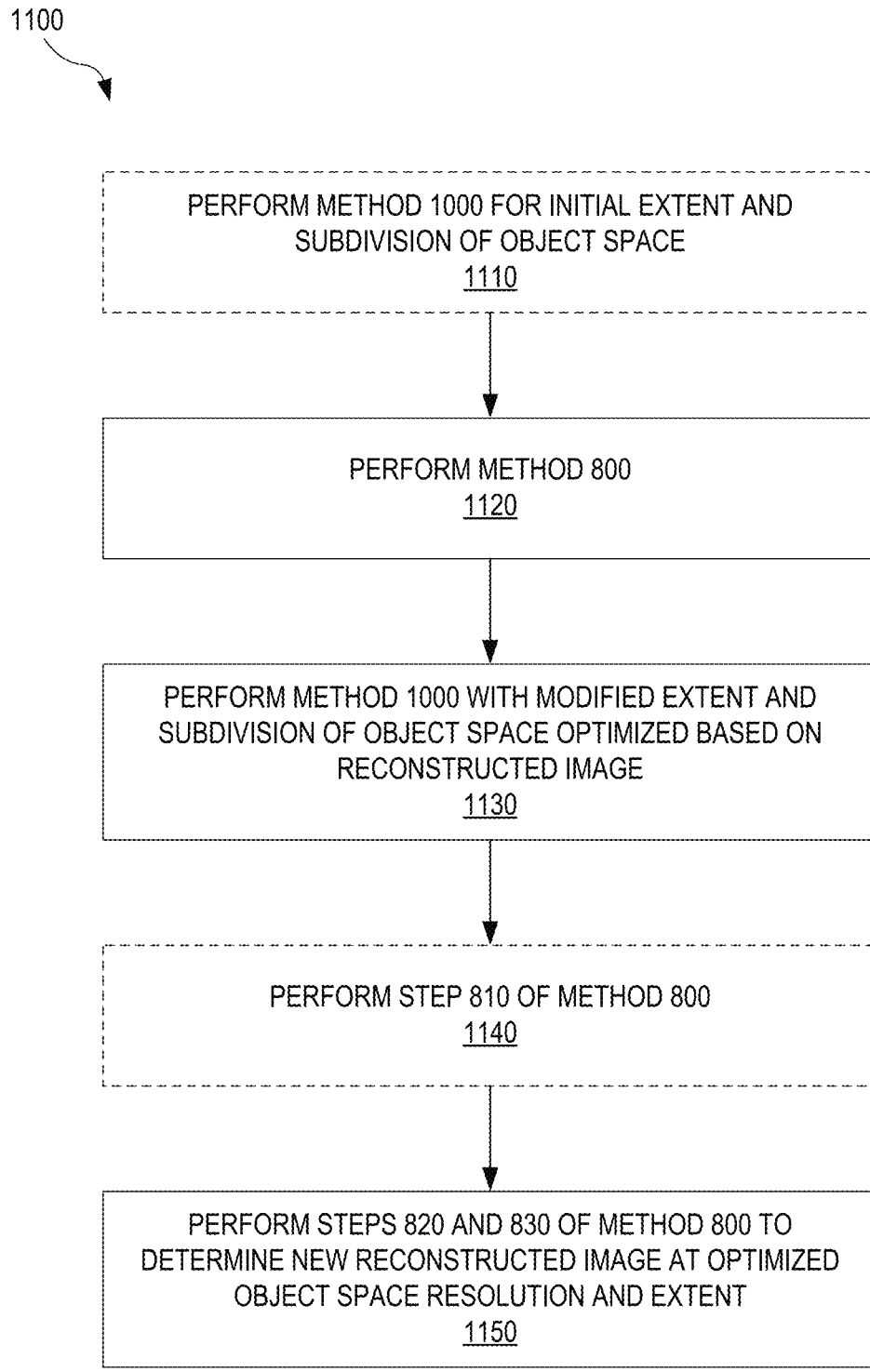
FIG. 11 illustrates a method for providing a dynamic field of view portion to the gamma ray imaging system of FIG. 1, according to an embodiment.

FIG. 11 illustrates one exemplary method 1100 for dynamically changing the resolution and extent of the analyzed field of view portion of gamma ray imaging system 600 (FIG. 6). This method may be used to focus the analysis on gamma sources detected within an initial field of view portion. For example, an initial data set is generated for a wide field of view portion. Through analysis of the wide field of view portion, a smaller field of view portion, located within the wide field of view portion, is identified as being of particular interest. The analysis and, optionally, data capture, are repeated with the full computational and storage capacity devoted to the smaller field of view portion. This produces an improved image of the area of interest. This method may be used in situations where one or more stationary gamma sources located within the field of view of gamma ray imaging system 600 (FIG. 6) warrant more detailed investigation. Another application is investigation of gamma sources that move within the field of view of gamma ray imaging system 600 (FIG. 6). In this case, the gamma sources may be tracked using a wide field of view portion, and analyzed in detail using a smaller field of view portion. By alternating between the wide field of view portion and a smaller field of view portion, which may shift for each iteration, detailed investigation of the gamma sources may be performed while the gamma sources are in motion.

In an optional step 1110, method 1000 (FIG. 10) is performed for an initial extent and subdivision of the object space. The object space is the analyzed field of view portion. For example, processor 610 (FIG. 6) performs step 1110 as discussed in connection with FIG. 10. Alternatively, step 1110 is performed externally to gamma ray imaging system 600 (FIG. 6). In embodiments of method 1100 where optional step 1110 is omitted, the output of method 1000 (FIG. 10), i.e., the conditional probabilities are preloaded to conditional probabilities 642 (FIG. 6). In a step 1120, method 800 is performed as discussed in connection with FIG. 8. This generates an initial reconstructed image of the object space with an initial extent and an initial resolution. In certain embodiments, step 830 of method 800 (FIG. 8) is performed according to method 900 (FIG. 9). In a step 1130, method 1000 (FIG. 10) is performed with a modified extent and subdivision of the object space. Step 1130 is, for example, performed by gamma ray imaging system 600 (FIG. 6) as discussed in connection with FIG. 10. The modified extent and subdivision is defined based on information in the reconstructed image determined in step 1120. In an optional step 1140, step 810 of method 800 (FIG. 8) is performed. This step is included in method 1100, for example, if a new data set is acquired by gamma ray imaging system 600 (FIG. 6). This may be relevant in cases where a longer data acquisition time is desired when interrogating the modified object space. In a step 1150, steps 820 and 830 of method 800 (FIG. 8) is performed, for example by gamma ray imaging system 600 (FIG. 6) as discussed in connection with FIG. 8. In embodiments including optional step 1140, step 1150 is performed on the new data set obtained in step 1140, optionally combined with the data set used in step 1120. In embodiments omitting optional step 1140, step 1150 is performed on the data set used in step 1120. Step 1150 is, for example, performed by gamma ray imaging system 600 (FIG. 6) as discussed in connection with FIG. 8.

Method 1100 may be extended to multiple iterations of the method, inclusion of additional small field of view portions to investigate multiple, spatially separated gamma source in greater detail, without departing from the scope hereof.

EXAMPLE I

Calculation of H, $H_{coded}$, and Evaluation of Coded Apertures

This example demonstrates calculation of the matrix H of probabilities of generating all possible combinations of measured quantities and the location of cell 275 (FIG. 2) of coded aperture 160 (FIGS. 1 and 2), conditional on all object space locations and energies. This matrix is discussed in connection with FIG. 10. In the present example, H is calculated using a Monte Carlo simulation. Any photon transport method may be used instead of a Monte Carlo simulation. The example further evaluates different arrangements of cells 275 (FIG. 2) of coded aperture 160 (FIGS. 1 and 2) using corresponding conditional probabilities $H_{coded}$, as discussed in connection with FIGS. 9 and 10.

In the present Monte Carlo simulation, Compton scattering occurs at a single plane, where only single scattering events are considered. At energies above 1.022 MeV, pair production in the Compton layer should be considered. By referring to NIST XCOM data, it may be seen that even up to 1.5 MeV, pair production contributes only about 0.3% of the events. For this reason, pair production is not included in the present simulations. Background events may include energies above 1.5 MeV in some special cases where short-lived isotopes or neutrons are present. These would be apparent by means of a 511 keV peak in the full-energy spectrum measured by full-energy detector 170 (FIGS. 1 and 2). This may be discriminated out if necessary.

At source energies of 1.5 MeV, Compton scattered electrons may have ranges in silicon up to 3 mm, which is comparable to the thickness of the Compton scattering layer 150 (FIGS. 1 and 2). If electrons escape, they do not deposit their full energy in the detector and this effect could contaminate the signals. However, the electrons that would be most likely to escape at those energies would have to have been deposited by scattering events that sent the scattered photon in a backward direction. These photons would not make it to the second detector, since they would have scattered through more than 90 degrees and most likely, closer to 180 degrees. A photon scattered through 90 degrees may be detected in the full-energy detector, but the electron would have half the original photon energy, a maximum of 0.75 MeV, and would be traveling nearly in the plane of the Compton detector, with a range of 1.5 mm. This effect may be calculated using a coupled photon-electron Monte Carlo simulation. The present simulations omit this effect since the effect is insignificant for a 2 mm thick silicon detector.

The present example considers an embodiment of Compton scattering layer 150 (FIGS. 1 and 2) that is square with a side length of 100 mm, on a 150 mm diameter wafer, with a thickness of 2-3 mm. Analysis has shown that for a silicon detector 2 mm thick, the interaction efficiency, i.e., the fraction of incident photons that scatter, ranges from 2.39% at 1.5 MeV to 6.53% at 150 keV for normally incident photons and 4.72% at 1.5 MeV to 12.6% at 150 keV for photons incident at an angle of π/3 radians from normal incidence. At these interaction rates, only considering single scattering events is a reasonable approximation. Alternative simulations may consider double scattering within the Compton detector. The results of such simulations may be used to identify the ideal thickness.

The present example considers an embodiment of coded aperture 160 (FIGS. 1 and 2) of a high-density material, such as a tungsten alloy. The simulation assumes an ideal mask, where all photons which hit the closed portions are completely blocked. In the present example, coded aperture 160 (FIGS. 1 and 2) is square with a side length of 100 mm, and is located at a distance of 50 mm from the Compton scattering layer.

The imaging theory uses the equation $$\langle I \rangle = H \times O, \quad \text{(Eq. 6)}$$

which is equivalent to Eq. 3, except that H and the coincidence event vector I included information about cells 275 (FIG. 2) of coded aperture 160 (FIGS. 1 and 2). The object vector, O, contains either 16 or 256 spatial bins with 16 energy bins for each. The spatial bins are determined by equally spaced angles from π/3 to −π/3 in both the x and y direction. With this geometry, off axis sources maintain the same efficiency at gamma ray imaging system 600 (FIG. 6), since the reduction in the projected area of at gamma ray imaging system 600 (FIG. 6) that the source sees cancels with the increased efficiency the off-axis source achieves when penetrating at gamma ray imaging system 600 (FIG. 6) at a non-normal angle. The energy bins are equally spaced from 150 keV to 1.5 MeV.

The coincidence event vector I is made up of four attributes, two for energy, each with 16 bins, and two for position, each with either 16 or 256 bins. The four attributes are energy and position in Compton scattering layer 150 (FIGS. 1 and 2), and energy and position in full-energy detector 170 (FIGS. 1 and 2). The position in full-energy detector 170 (FIGS. 1 and 2) is taken to be the position of the cell 275 (FIG. 2) of coded aperture 160 (FIGS. 1 and 2). Despite the design described here not having position information in coded aperture 160 (FIGS. 1 and 2), the simulation retains this information for validation and debugging as well as to compare results and performance to a theoretical, conventional Compton camera. Thus, the image vector contains either 64 k or 16M entries.

The program simulates each photon through ray tracing. To generate H, each possible incoming direction and energy is simulated several million times. The program cycles through each pixel 270 (FIG. 2) of Compton scattering layer 150 (FIGS. 1 and 2), selecting random interaction points within pixel 270. The program then samples the probability distribution to select an outgoing direction and corresponding energy. The projection of the probability distribution on coded aperture 160 (FIGS. 1 and 2) is then determined and the event is scored in the appropriate cell 275 (FIG. 2) thereof. This maps into a column of H as probabilities of a given object photon creating a specific coincidence event. With the number of pixels and energy bins growing, the dimensions of H quickly grow to sizes difficult to manipulate even with powerful computers. Although this matrix only needs to be generated once, it requires the bulk of the computation time needed to simulate the system.

The test object O is run through the same Monte Carlo simulation, but with its specific locations, source strengths and energies. These results are then run through a reconstruction computation. For the case of the smaller dimensional simulation, reconstructions were done with both least squares estimation and maximum likelihood. Comparisons of these two methods are discussed below. For the larger dimensional case, calculating the Gramian H'×H necessary to perform a least squares reconstruction proved to be unreasonably difficult, due to the large size of the matrix and the limits of the computer to store and manipulate such large matrices. Therefore, the reconstruction in the larger dimensional case was done only using MLEM.

In the present simulations, H is either a (64 k×256) or a (16M×4 k) matrix. When coded aperture 160 (FIGS. 1 and 2) is used, all of the counts in the open half (8 out of 16 or 128 out of 256) of the full-energy position bins are summed into a single bin. This reduces the dimension of H to (4 k×256), or (64 k×4 k).

All Monte Carlo simulations were built within Matlab. The modular design of the code allows for quick changes in all design parameters, such as numbers of pixels, energy bins and relative distances between detectors. In addition, the program was written with the intention of being able to modify and integrate more accurate physics as each version of it proved valid. This allows for ease in implementation of more accurate probabilities of interaction as we explore possible detector materials and dimensions. Other Monte Carlo programs, such as Geant or MCNP may be used to implement the simulation, though the scoring scheme is very cumbersome to model. Building a code for this specific purpose simplifies the rapid testing of multiple configurations without significant time spent reprogramming the geometry.

The Compton scattering cross sections $\Sigma_c(k_0)$ in the simulation is governed by the Klein-Nishina formula:

$$\frac{d\sum_c(k_0)}{dk} = \frac{X_0 n\pi r_0^2 m}{k_0^2}\left[\frac{\left(\frac{C_1}{\varepsilon}+C_2\right)}{\varepsilon}+C_3+\varepsilon\right], \quad \text{(Eq. 7)}$$

where $X_0$=radiation length (cm), n=electron density (electron/cm$^3$), $r_0$=classical electron radius (cm$^2$), m=electron rest energy (MeV), $k_0$=incident photon energy (MeV), k=scattered photon energy (MeV), $\epsilon$=k/$k_0$, $C_1$=$(k'_0)^2$, $k'_0$=$k_0$/m, $C_2$=1−2(1+$k'_0$)/$(k'_0)^2$, and $C_3$=(1+2 $k'_0$)/$(k'_o)^2$.

In order to incorporate the appropriate scattering cross sections into the model, the solution used in EGS4 code (W. R. Nelson, H. Hirayama, and D. W. Rogers, "THE EGS4 CODE SYSTEM," SLAC-0265, 1985) was found to be very efficient and easy to implement. The code, as implemented in the present simulations, uses the cross section $$\frac{d\sum_c}{d\varepsilon} = \frac{X_0 n\pi r_0^2 m}{k_0^2}\left[\frac{1}{\varepsilon}+\varepsilon\right]\left[1-\frac{\varepsilon\sin^2\theta}{1+\varepsilon^2}\right] \propto f(\varepsilon)g(\varepsilon), \quad \text{(Eq. 8)}$$

where the differential cross section may be defined as proportional to two functions of $\in$. Through these functions and a change of variables, random numbers are drawn uniformly over the interval (0,1) in order to sample secondary photon energies.

Due to the simplicity of the Monte Carlo simulation, which includes only a single scatter, the only validation necessary is of the Klein-Nishina scattering distribution. The coding of this method of calculating the scattering distribution was verified to provide accurate results.

The present simulation is configured for far-field monitoring to image a two-dimensional object space. Thus, reconstructions represent objects by angles in horizontal and vertical axes and with given energy, but with no distance information.

From simulations with a 4×4 pixel Compton scattering layer 150 (FIGS. 1 and 2) and a 4×4 cell coded aperture 160 (FIGS. 1 and 2), it was determined that the most consistent results and highest efficiency are obtained with a coded aperture 160 (FIGS. 1 and 2) with 50% of cells 275 (FIG. 2) open. The coded aperture simulated was modeled as ideal. This means it has no thickness and is 100% opaque to all photons that strike the closed portions. Once the materials and dimensions are determined, absorption, transmission and scattering may be incorporated to provide results that are more realistic. However, the positioning of coded aperture 160 (FIGS. 1 and 2) behind Compton scattering layer 150 (FIGS. 1 and 2) also has the advantage of only being seen by scattered photons. This means that all the photons, getting to coded aperture 160 (FIGS. 1 and 2), that are of interest, have scattered at least once in Compton scattering layer 150 (FIGS. 1 and 2) and have lost some of their energy, decreasing the effective transmission through the shielded portions of the mask.

In order to quantitatively evaluate different masks in the 4×4 pixel configuration, both the condition number and trans-information of H were calculated (see Table I). The condition number is a measure of the extent to which errors are amplified in the image reconstruction. It is defined as the ratio of the largest singular value of H to the smallest. This means the larger the condition number, the more sensitive a solution is to changes the input.

TABLE I

| | Condition # | | Trans-information |
|---|---|---|---|
| | H | H' × H | H |
| H full | 63.24 | 4.0 × 10$^3$ | 0.9352 |
| H1$_{coded}$ | 171.92 | 3.0 × 10$^4$ | 0.3905 |

TABLE I-continued

| Condition # | | Trans-information |
|---|---|---|
| H | H' × H | H |
| H2$_{coded}$ 189.71 | 3.6 × 10$^4$ | 0.3947 |
| H3$_{coded}$ 263.25 | 6.9 × 10$^4$ | 0.4279 |

For a maximum likelihood (MLEM) reconstruction, the trans-information may be a more relevant figure of merit and is shown in the last column of Table I. Generally, the trans-information is the entropy of the observed values as reduced by the conditional entropy characterizing the channel of communication, which may be expressed as $$TI = \sum_i \sum_j p(x_i, y_j) \log\left[\frac{p(y_j, x_i)}{p(y_j)}\right]. \quad \text{(Eq. 9)}$$

The trans-information is a measure of how much information is transmitted by H. While a single near-zero value in H is sufficient to yield a very large condition number, the trans-information considers the overall effect of H.

In Table I, "H full" represents the full (64 k×256) matrix with all pixel information retained and H1$_{coded}$ through H3$_{coded}$ are the coded-aperture filtered versions (4 k×256) with different mask patterns. H1$_{coded}$ and H3$_{coded}$ represent reconstruction matrices with the largest and smallest condition numbers when considering all possible coded aperture patterns with 50% open over the entire aperture as well as within each of the 4 quarters. H2$_{coded}$ has a condition number in the center of the range.

Figure 12:
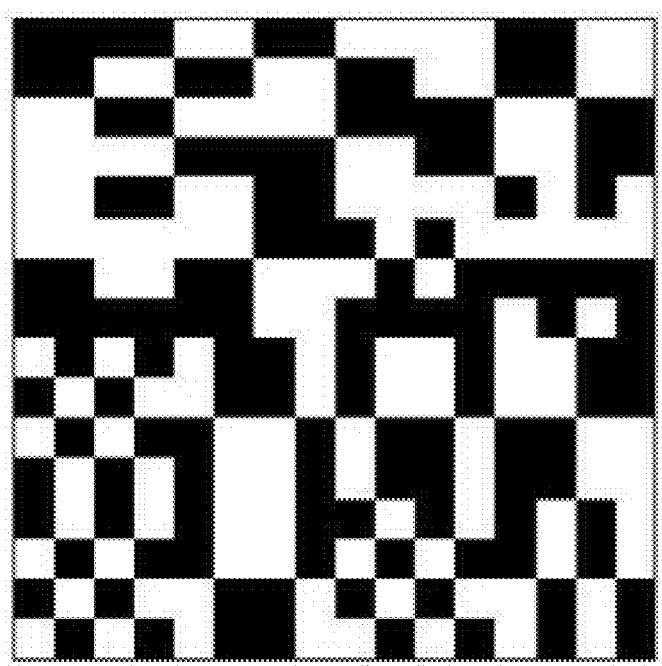
FIG. 12 illustrates an exemplary layout of the coded aperture of the gamma ray imaging system of FIG. 1, according to an embodiment.

Arrays up to 16×16 pixels in each layer, together with 4-bit energy resolution, in each layer, have also been implemented using binned data acquisition. Much larger arrays may be used with list-mode data acquisition/image reconstruction. The larger coded aperture was generated manually, with restrictions in the openings that ensured that 50% of the entire pattern was open, as was each 4×4 group of squares. This coded aperture, which is an embodiment of coded aperture 160 (FIGS. 1 and 2), is illustrated in FIG. 12 as coded aperture 1200. More coded aperture patterns may be tested to find the most effective pattern. Other coded aperture, such as Uniformly Redundant Arrays (URAs) and Modified URAs (MURA) may also be used.

Tests using a 4×4 pixel configuration in Compton scattering layer 150 (FIGS. 1 and 2) and coded aperture 160 (FIGS. 1 and 2), with 4-bit energy resolution can easily be run on a personal computer.

The 16×16 pixel configuration, as used for coded aperture 1200 (FIG. 12), requires substantial computing time and storage allocation for calculation of H. The UA Research Computing High Performance Computing (HPC) at the University of Arizona was used for this. It is an SGI Altix ICE 8400 featuring 2.66 GHz Xeon Westmere-EP Dual 6-core processors. Each node has 12 cores with 2 GB of memory per core. In order to calculate H with sufficient statistics, the simulation utilized 120 cores to simulate 1.6×10$^{10}$ photons. Every incoming angle and energy combination was simulated approximately 4×10$^5$ times. This simulation took approximately 10 hours to run. The dimensions of H, for the largest system tested, are 16M×4 k and require 700 MB to store, even with Matlab's sparse array storage, which reduces the size by only storing the non-zero numbers and their indices.

EXAMPLE II

Image Reconstruction Results

This example demonstrates reconstruction of an image of gamma source configurations, illustrated for theoretical gamma source configurations. Coincidence events are simulated based on the theoretical gamma source configuration. The image reconstruction is performed using the methods of FIGS. 8 and 9. The specific system parameters are as discussed in Example I, and the same simulation methods are utilized.

The principle advantage of simulating and scoring the location information from full-energy detector 170b (FIGS. 1 and 2) is that a conventional Compton camera can be simulated to compare results. The imaging performance of the conventional Compton camera and gamma ray imaging system 110 (FIG. 1) were tested in their 4×4 pixel configuration using the input test object 1300 shown in FIG. 13A. A higher resolution version, input test object 1310 shown in FIG. 13B, was also used for gamma ray imaging system 110. The conventional Compton camera could not be simulated in the high-resolution case because of the huge number of bins and the limitations in computing resources when manipulating the large data set. Because of the object's two-dimensional position (two orthogonal angles) and one-dimensional energy, the object space was mapped in a way that could allow this three-dimensional data to be displayed in a single, two-dimensional image. Each position pixel is subdivided into 4×4 pixels representing the various energy bins.

Figure 13A:
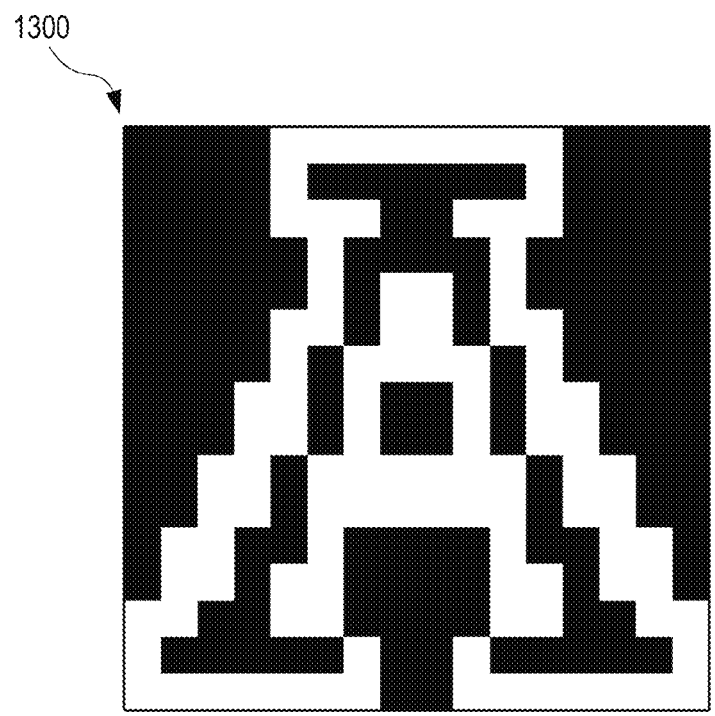
FIGS. 13A and 13B show test objects used to simulate the performance of one exemplary embodiment of the gamma ray imaging system of FIG. 1, according to an embodiment.
Figure 13B:
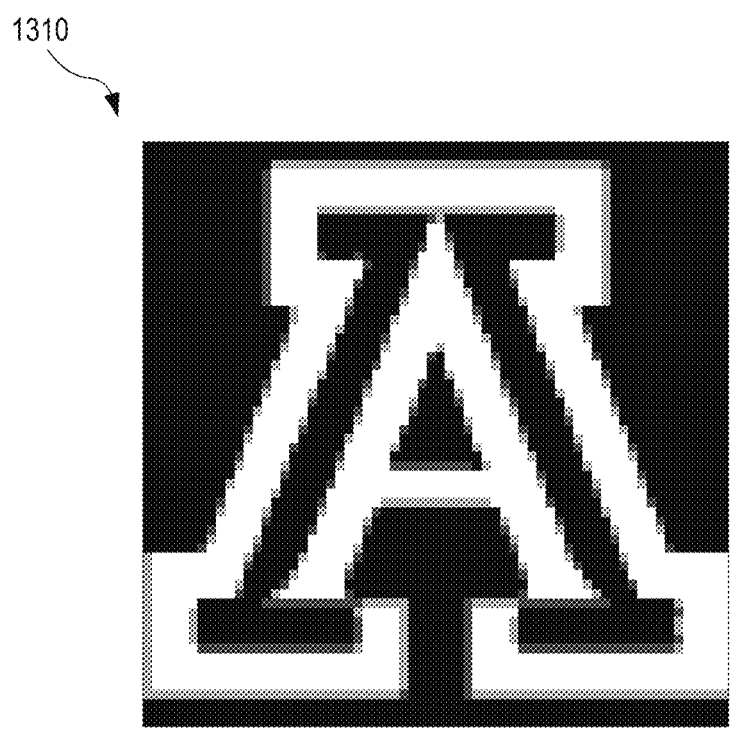
Figure 14:
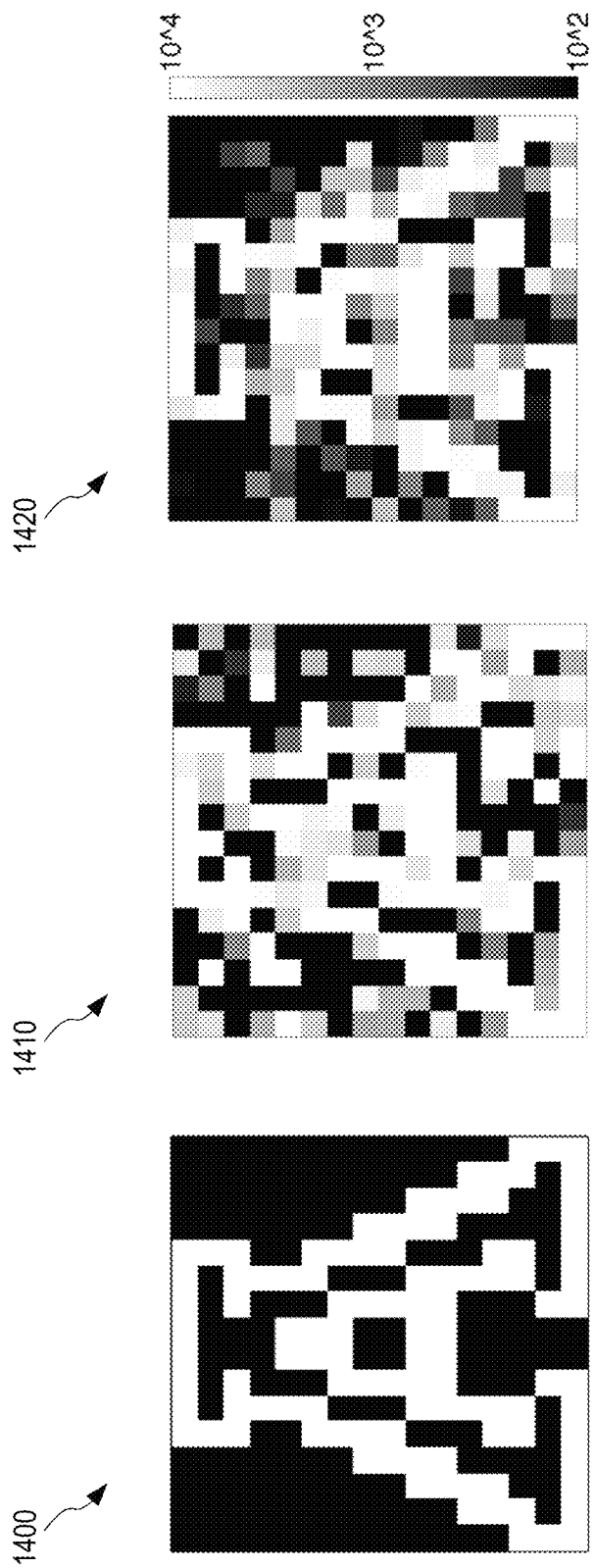
FIG. 14 compares image reconstruction results for the gamma ray imaging system of FIG. 1 obtained using two different embodiments of the image reconstruction method of FIG. 9, according to an embodiment.

FIG. 14 shows reconstructed images 1410 and 1420 of an artificial test object 1400 (same as test object 1300 of FIG. 13A). In order to reduce superfluous computing, the current computing model only simulates events that interact in Compton scattering layer 150 (FIGS. 1 and 2). This is a standard acceleration technique for Monte Carlo simulations. The number of events, N$_i$, in the test objects are the number of photons incident on Compton scattering layer 150 (FIGS. 1 and 2) with 100% detection and scattering efficiency, while the number of events, N$_o$, in the image reconstructions are the number of events recorded in the image space. For gamma ray imaging system 110 (FIGS. 1 and 2), the image space is the space of coincidence events composed of (a) position and energy of Compton scattering events in Compton scattering layer 150 (FIGS. 1 and 2), and (b) the full energy of scattered gamma photons produced thereby. N$_i$ and N$_o$ are not the same, because not all photons scattered in Compton scattering layer 150 (FIGS. 1 and 2) reach full-energy detector 170 (FIGS. 1 and 2). The source strength of a given number of photons detected may be calculated using the absolute efficiency of the detector discussed in Example III.

For test object 1400, N$_i$=1.06×10$^6$. Reconstructed image 1410 represents a reconstruction for gamma ray imaging system 110 (FIGS. 1 and 2) using the LS method, discussed in connection with step 950 of FIG. 9, with N$_o$=117,891. Reconstructed image 1420 represents a reconstruction for gamma ray imaging system 110 (FIGS. 1 and 2) using the MLEM method, discussed in connection with step 950 of FIG. 9, also with N$_o$=117891.

When considering the lowest energy regime, it is important to note that the image reconstructions generated in the present example, show the case where the lowest energy bin of either detector had a lower bound of zero. In the more realistic point source cases discussed in Example IV, the lower bound is set to 50 keV in Compton scattering layer 150 (FIGS. 1 and 2), and 100 keV in full-energy detector 170 (FIGS. 1 and 2). Reconstructed images 1410 and 1420, together with further reconstructed images not shown in FIG. 14, illustrate that the MLEM method yield similar results at high count rates, and more accurate results at lower count rates, as compared to the LS method. The similarity of LS and MLEM reconstructions at high count rates is expected, because the LS method is maximum likelihood for a normal distribution of counts. The true distribution is Poisson, however, and the MLEM method used here uses the true Poisson-likelihood. The normal distribution approximates to the Poisson distribution when the counts in each image bin are large enough.

Figure 15:
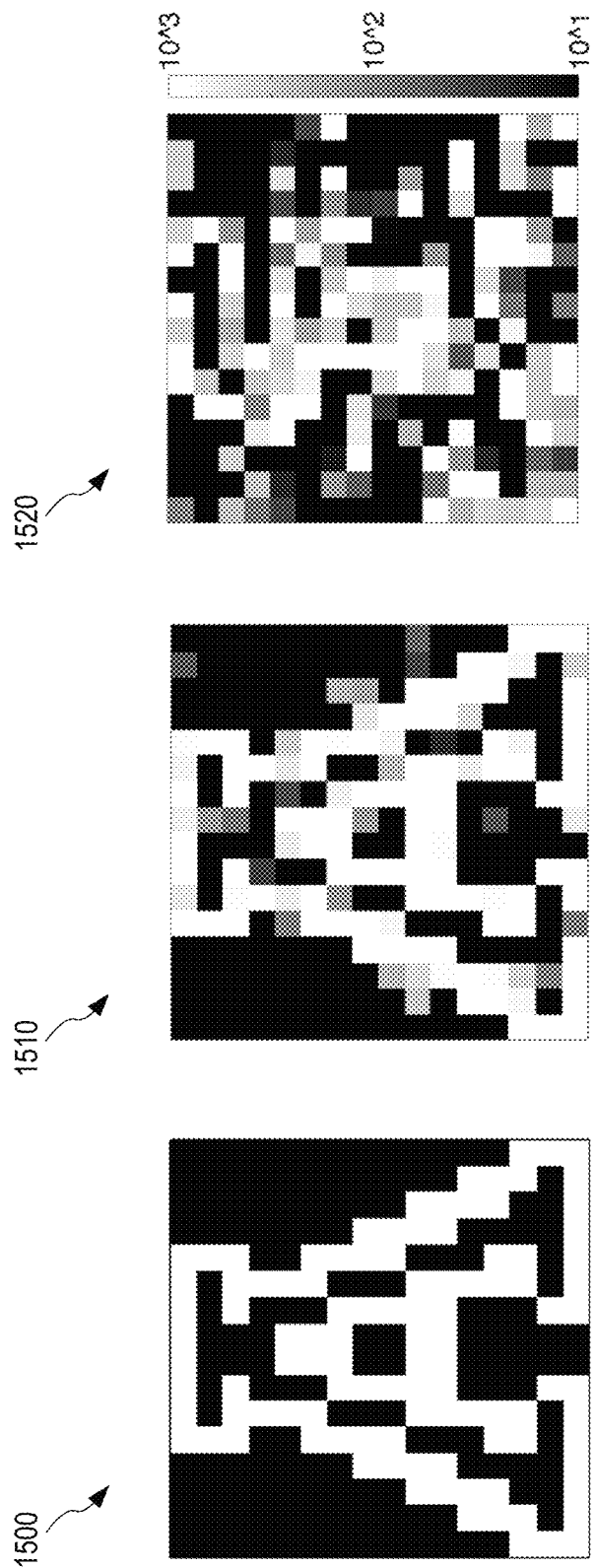
FIG. 15 compares image reconstruction results for the gamma ray imaging system of FIG. 1 to those of a conventional Compton camera, in a low count-rate situation, obtained using the image reconstruction method of FIG. 9, according to an embodiment.
Figure 16:
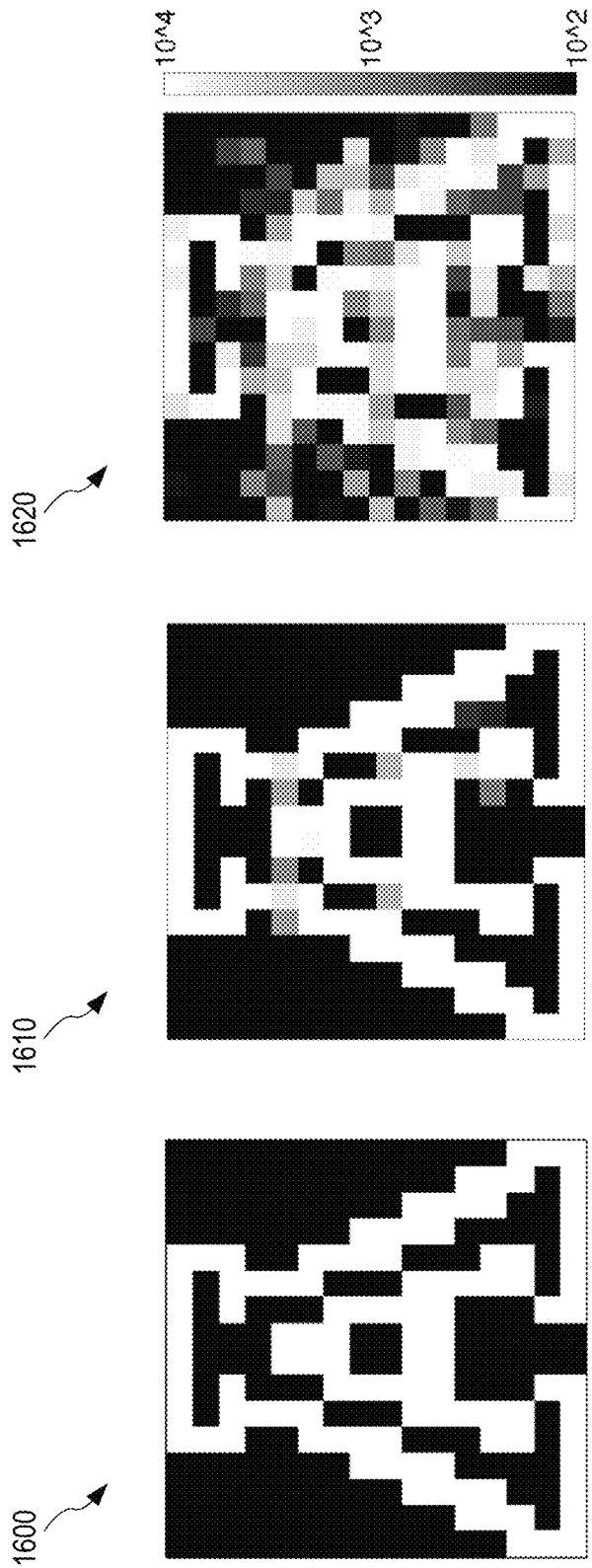
FIG. 16 compares image reconstruction results for the gamma ray imaging system of FIG. 1 to those of a conventional Compton camera, in a medium count-rate situation, obtained using the image reconstruction method of FIG. 9, according to an embodiment.
Figure 17:
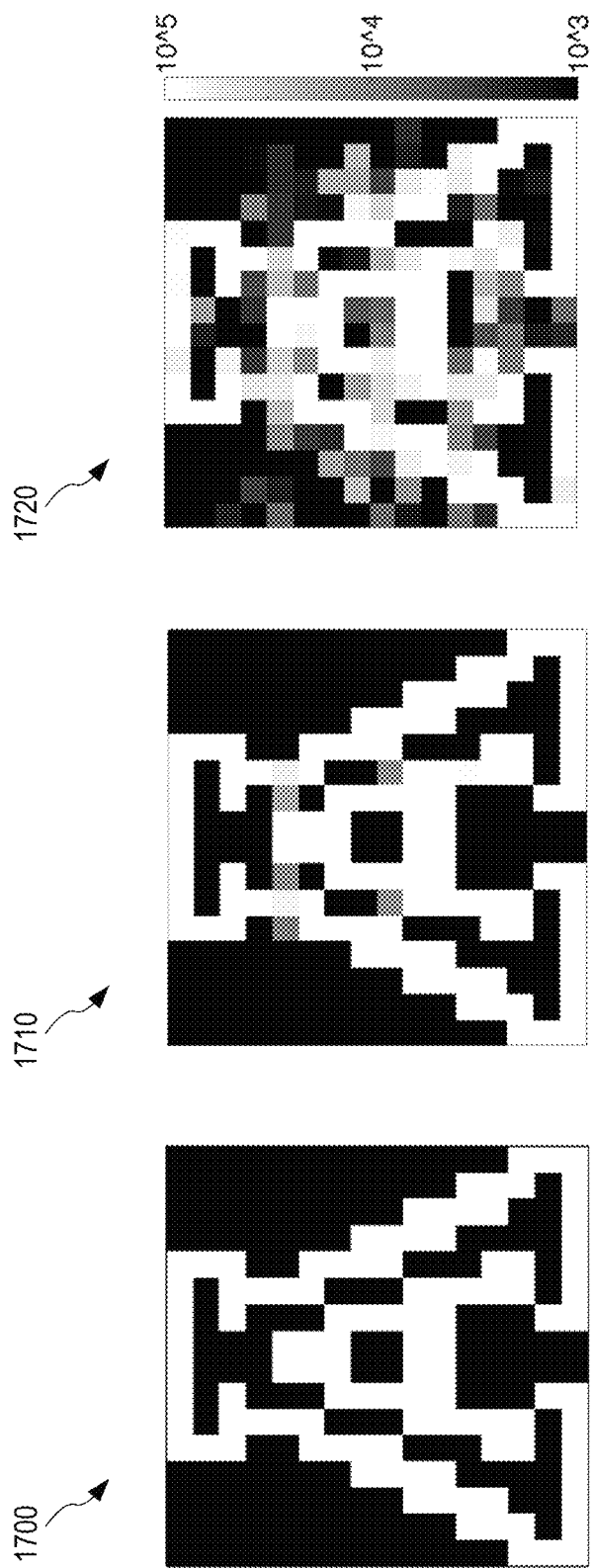
FIG. 17 compares image reconstruction results for the gamma ray imaging system of FIG. 1 to those of a conventional Compton camera, in a high count-rate situation, obtained using the image reconstruction method of FIG. 9, according to an embodiment.

FIGS. 15, 16 and 17 shows image reconstructions at various count rates, for both the conventional Compton camera and gamma ray imaging system 110 (FIGS. 1 and 2). The reconstructed images shown in FIGS. 15, 16 and 17 are based on the MLEM method discussed in connection with step 950 (FIG. 9). The conventional Compton camera was modeled as a modification of gamma ray imaging system 110 (FIGS. 1 and 2), in which a pixelated full-energy detector directly replaced coded aperture 160 (FIGS. 1 and 2) and non-pixelated full-energy detector 170 (FIGS. 1 and 2).

FIG. 15 shows reconstructed images 1510, for the conventional Compton camera, and 1520, for gamma ray imaging system 110 (FIGS. 1 and 2), of an artificial test object 1500. For test object 1500, identical to test object 1300 of FIG. 13A, $N_i=1.06\times10^5$. For reconstructed image 1510, $N_o=23,510$, and for reconstructed image 1520, $N_o=11,823$. FIG. 15 illustrates a low count-rate situation.

FIG. 16 shows reconstructed images 1610, for the conventional Compton camera, and 1620, for gamma ray imaging system 110 (FIGS. 1 and 2), of an artificial test object 1600. For test object 1500, identical to test object 1300 of FIG. 13A, $N_i=1.06\times10^6$. For reconstructed image 1610, $N_o=235,099$, and for reconstructed image 1620, $N_o=117,891$. FIG. 16 illustrates a medium count-rate situation.

FIG. 17 shows reconstructed images 1710, for the conventional Compton camera, and 1720, for gamma ray imaging system 110 (FIGS. 1 and 2), of an artificial test object 1700. For test object 1700, identical to test object 1300 of FIG. 13A, $N_i=1.06\times10^7$. For reconstructed image 1710, $N_o=2,349,660$, and for reconstructed image 1720, $N_o=1,175,713$. FIG. 17 illustrates a high count-rate situation.

At high count rate (FIG. 17), results for gamma ray imaging system 110 (FIGS. 1 and 2) approach the conventional Compton reconstruction, despite the loss of the pixel information and approximately half of the number of events. At low count rates (FIG. 15), however, the coded aperture produces noticeably inferior results. By comparing reconstructed images 1520 (FIG. 15), 1620 (FIG. 16), and 1720 (FIG. 17), it is evident that gamma ray imaging system 110 (FIGS. 1 and 2) requires a factor of about 100 more counts to reconstruct an equal image, as compared to the conventional Compton camera.

This comparison between the conventional Compton camera and gamma ray imaging system 110 (FIGS. 1 and 2) demonstrates that the latter is capable of achieving similar resolution, but that more counts are needed. This could be expected by comparing the trans-information numbers of the respective H-matrices (Table I). It should be remembered, however, that the detection efficiency actually achievable with a pixelated full-energy detector is much lower than that of a thick non-pixelated second detector. The comparisons in FIGS. 15, 16 and 17 do not take this into account.

Figure 18:
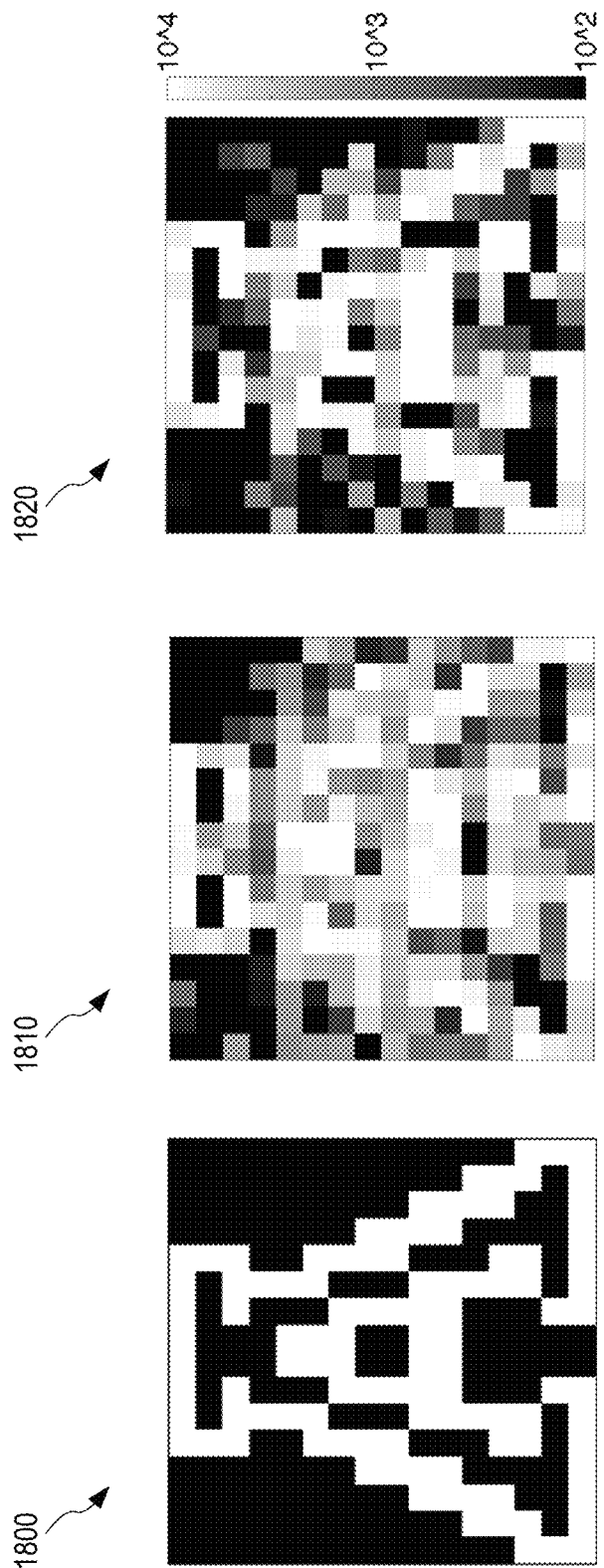
FIG. 18 compares image reconstruction results for the gamma ray imaging system of FIG. 1 to those of an equivalent system without a coded aperture, obtained using the image reconstruction method of FIG. 9, according to an embodiment.

FIG. 18 compares gamma ray imaging system 110 (FIGS. 1 and 2) to the identical system without coded aperture 160 (FIGS. 1 and 2) but with the same non-pixelated full-energy detector 170 (FIGS. 1 and 2). This is equivalent to a conventional Compton camera but with no position information retained in the pixelated full-energy detector. FIG. 18 shows a test object 1800, identical to test object 1300 of FIG. 13A, with $N_i=1.06\times10^6$, which corresponds to a medium count-rate situation. A reconstructed image 1810 is a reconstruction of test object 1800 for the system without coded aperture 160 (FIGS. 1 and 2) with $N_o=117,891$. A reconstructed image 1820 is a reconstruction of test object 1800 for gamma ray imaging system 110 (FIGS. 1 and 2) with $N_o=235,099$. Both reconstructions are based on the MLEM method discussed in connection with step 950 of FIG. 9.

In this comparison, the image vectors of both of the systems contain the same number (4 k) of attributes, and the matrices of conditional probabilities are both 4 k×256. With the presence of coded aperture 160 (FIGS. 1 and 2), despite the loss of half of the detected events, the improvement in image quality is clear. This demonstrates the usefulness of the mask and shows its capability as an alternate to a configuration with a pixelated full-energy detector. On the other hand, some information is obtained using the system without coded aperture 160 (FIGS. 1 and 2). This is due to the fact that the finite size of full-energy detector 170 (FIGS. 1 and 2) restricts the possible propagation angles between Compton scattering layer 150 (FIGS. 1 and 2) and full-energy detector 170 (FIGS. 1 and 2). In fact, this system is identical to an embodiment of gamma ray imaging system 110 (FIGS. 1 and 2), where all cells 275 (FIG. 2) of coded aperture 160 (FIGS. 1 and 2) have 100% transmission.

Figure 19:
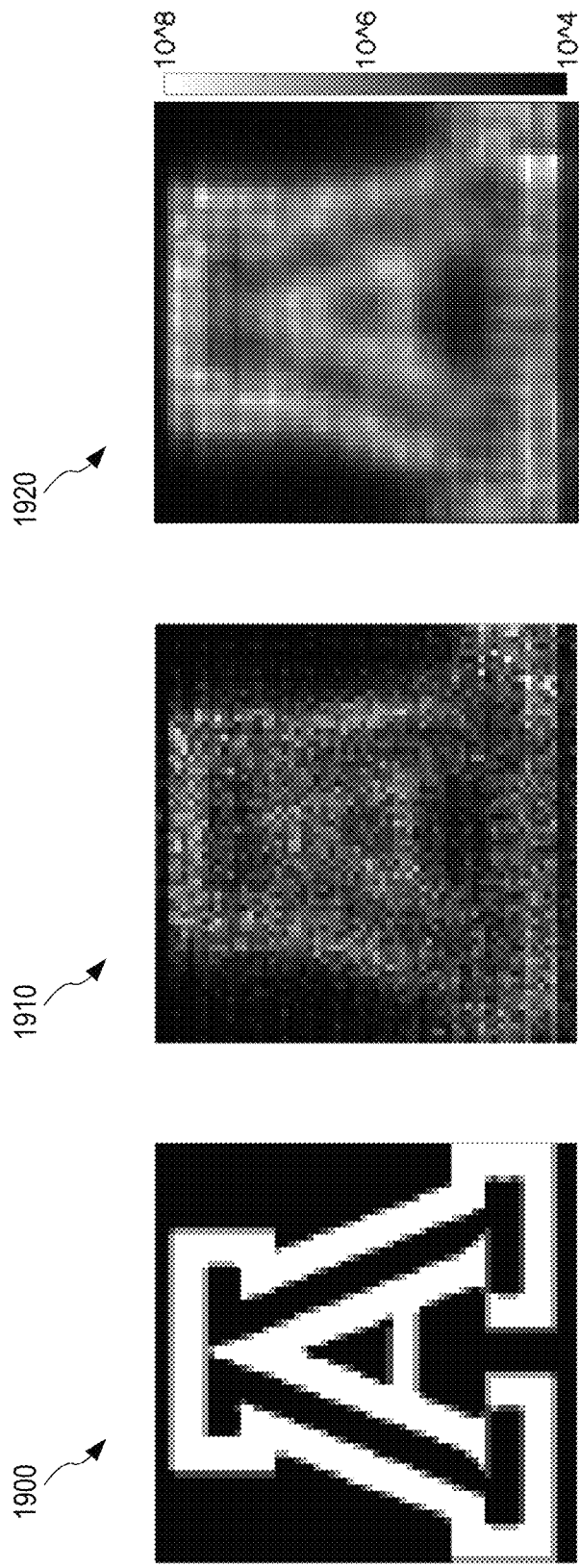
FIG. 19 shows image reconstruction results for the gamma ray imaging system of FIG. 1 in a high-resolution case, obtained using the image reconstruction method of FIG. 9 with and without incorporating a blurring kernel, according to an embodiment.

FIG. 19 shows reconstructed images 1910 and 1920, for gamma ray imaging system 110 (FIGS. 1 and 2), of a higher-resolution, artificial test object 1900. For test object 1900, identical to test object 1310 of FIG. 13B, $N_i=1.06\times10^8$. For reconstructed images 1910 and 1920, $N_o=182,271,094$. Both reconstructed images 1910 and 1920 have been generated using the MLEM method discussed in connection with step 950 of FIG. 9. The reconstruction of reconstructed image 1920 further included a blurring kernel to help counter the tendency (dark-sky effect) towards delta functions during MLEM reconstructions. The dark-sky effect comes about with non-regularized MLEM reconstructions when too many iterations are done, as discussed in connection with step 950 (FIG. 9). This effect may also be countered using a regularization factor.

EXAMPLE III

Detection Efficiency

The current Monte Carlo simulation does not directly calculate the detection efficiency of gamma ray imaging system 110 (FIGS. 1 and 2) because full-energy detector 170 (FIGS. 1 and 2) is not modeled, but rather treated as a black detector of full-energy events. Also, the first interaction probability in Compton scattering layer 150 (FIGS. 1 and 2) is not calculated, since only incident photons that undergo a Compton scattering event are considered. These factors are relatively easy to estimate, however, using simple assumptions.

When considering the detection efficiency for detection of $^{137}$Cs gamma rays, at 662 keV, the following approximate values may be used. Full-energy detection of Compton scattered photons, for energies less than 662 keV easily has a full-energy efficiency of 70%, with the use of a large scintillator crystal. The Compton efficiency of a 2 mm thick silicon detector, for normally incident photons at 662 keV, is 3.4%. A simulation gives an efficiency of 10.2% for detection of a Compton-scattered photon in full-energy detector 170 (FIGS. 1 and 2) through coded aperture 160 (FIGS. 1 and 2). Combining these values, an intrinsic efficiency of the system, for normally incident $^{137}$Cs photons, of $2.4 \times 10^{-3}$ is found.

The geometrical efficiency of a 100 cm$^2$ detector, for a point source at a 100 m distance therefrom, is $(1/4\pi) \times 10^{-6} \approx 8.0 \times 10^{-8}$. Thus, the overall efficiency for detection of a point source of $^{137}$Cs, at a distance of 100 m, is $1.94 \times 10^{-10}$. The count rate from a 1 Curie (Ci) source, which equals $3.7 \times 10^{10}$ Becquerel (Bq), would be 7.2 counts per second, or 4320 counts in 10 minutes.

The above estimate does not account for attenuation in air. At a distance of 100 m, this corresponds to a transmission factor of approximately 37.5%.

EXAMPLE IV

Detection of Point Sources

This example demonstrates reconstruction of an image of gamma source configurations, illustrated for theoretical gamma source configurations. Coincidence events are simulated based on the theoretical gamma source configuration. The image reconstruction is performed using the methods of FIGS. 8 and 9. The gamma sources considered in the present example are point sources. The specific system parameters are as discussed in Example I, and the same simulation methods are utilized.

The local dose rate, from directly transmitted gamma rays, at a distance of 100 m from a 1 Ci source ($3.7 \times 10^{10}$ Bq) of $^{137}$Cs is approximately 3 μSievert/hour (0.03 millirem/hour). This can be compared with an average gamma background rate of 1 μSievert/hour, which is approximately 80 millirem/yr, a typical natural photon exposure level.

The environmental background of photon radiation was represented using a simplified model, in which it was assumed that the photon flux per unit energy is inversely proportional to photon energy. This approximates the true spectrum for multiply scattered and cosmic ray photons, but does not represent the discrete energies from natural activity. Scattered photons in the environment have an approximately flat energy flux spectrum (white noise). For this reason, it is advantageous to plot photon spectra as energy flux densities instead of photon number densities. The background photon flux was also assumed to be isotropic.

The total background photon flux was normalized to give a dose rate of 1 tSievert/hour, from the photon flux between 150 keV and 1500 keV. The dose calculations in this example were done assuming that the dose rate D (rem/hr) at distance R (m) and transmission factor T, from a point source of strength C (Ci), emitting $E_\gamma$ average photon energy per disintegration is:

$$D = 0.52 \times E_\gamma \times \frac{C}{R^2} \times T. \quad \text{(Eq. 10)}$$

This approximation is valid for the range of energies considered in this example. An equivalent formula was used for the background photon flux.

Figure 20:
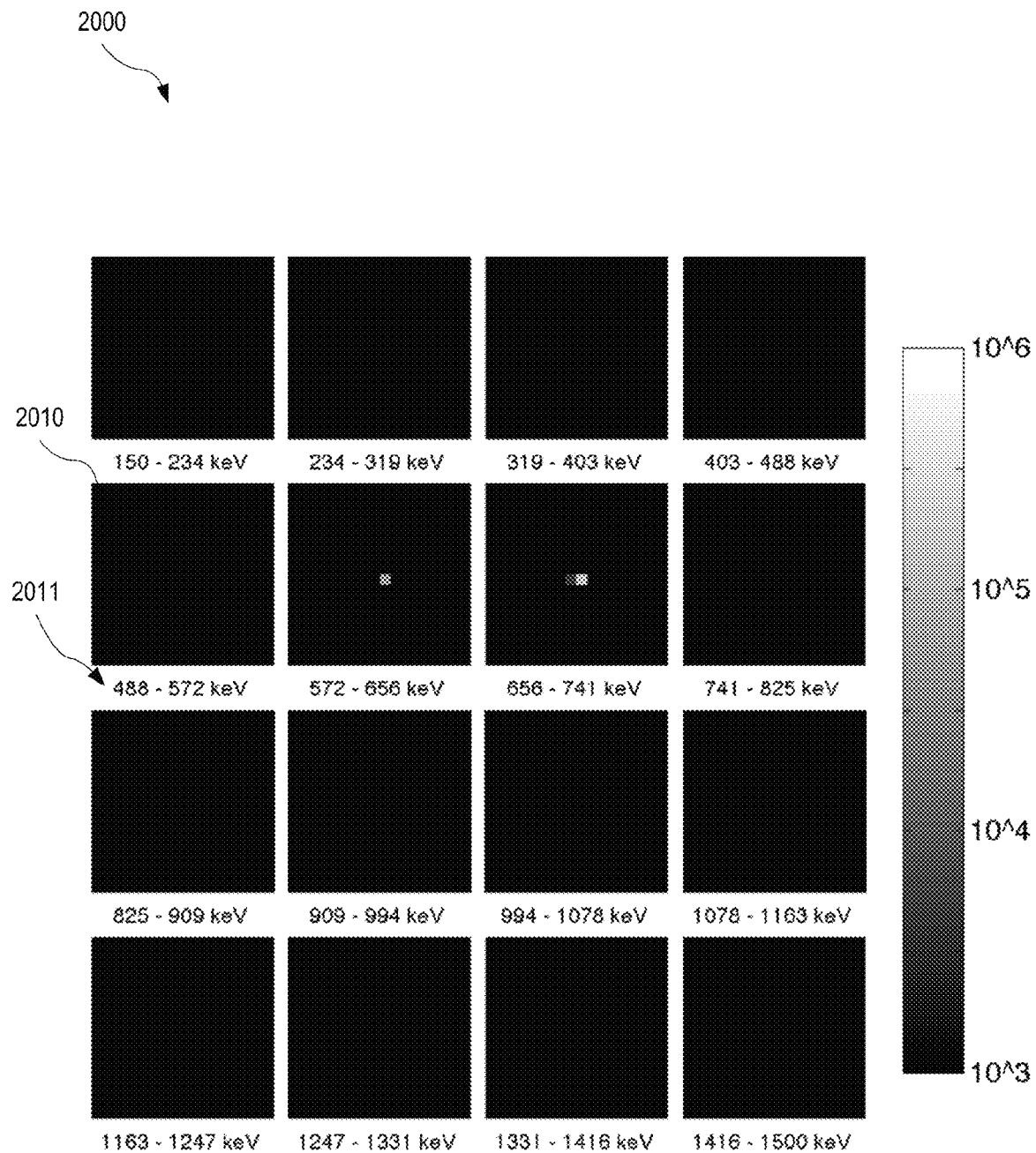
FIG. 20 shows image reconstruction results for a single point source viewed by the gamma ray imaging system of FIG. 1, obtained using the image reconstruction method of FIG. 9, according to an embodiment.

FIG. 20 shows a reconstructed image 2000 of a typical source, a $^{137}$Cs source located at a distance of 100 m. The $^{137}$Cs source and associated coincidence events are simulated. Assuming an image acquisition time of 10 minutes, the recorded number of events associated with the reconstructions corresponds to source strengths from approximately 64 mCi ($2.37 \times 10^9$ Bq) to 6.4 Ci ($2.37 \times 10^{11}$ Bq).

In FIG. 20, each sub-image 2010 (only one sub-image labeled in FIG. 20) is an energy slice that represents the spatial image of the object space for a given gamma source energy bin 2011. The energy flux scale displayed is logarithmic, spanning a three decade range, from $10^3$ to $10^6$ keV per spatial bin of the object space.

Figure 21:
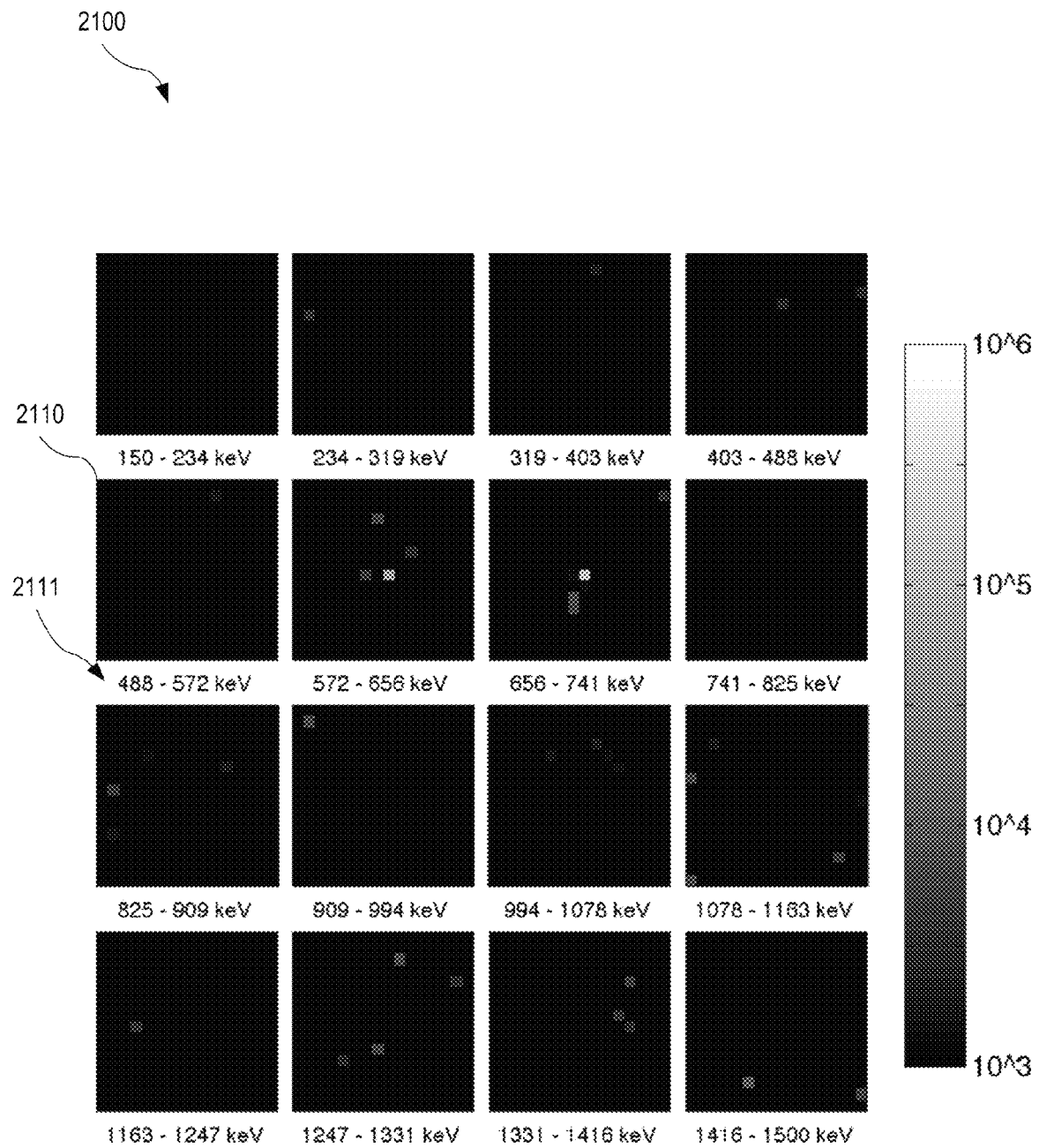
FIG. 21 shows image reconstruction results for a single point source, together with natural background, viewed by the gamma ray imaging system of FIG. 1, obtained using the image reconstruction method of FIG. 9, according to an embodiment.

FIG. 21 is equivalent to FIG. 20, except that natural background is included. FIG. 21 shows a reconstructed image 2100 as a series of sub-images 2110 for a respective series of energy bins 2111. Even in the lowest activity case, the correct energy and position is reproduced, with a spatial uncertainty of better than 7.5°, which is the spatial granularity of the object vector O. The smaller the detectable granularity, the larger the signal to noise ratio enhancement relative to an omnidirectional detector. For the 7.5° by 7.5° square pixel in this system, the signal to noise ratio enhancement is approximately 730:1. It is apparent that the spatial resolution is actually finer than the granularity assigned to the object space.

Figure 22:
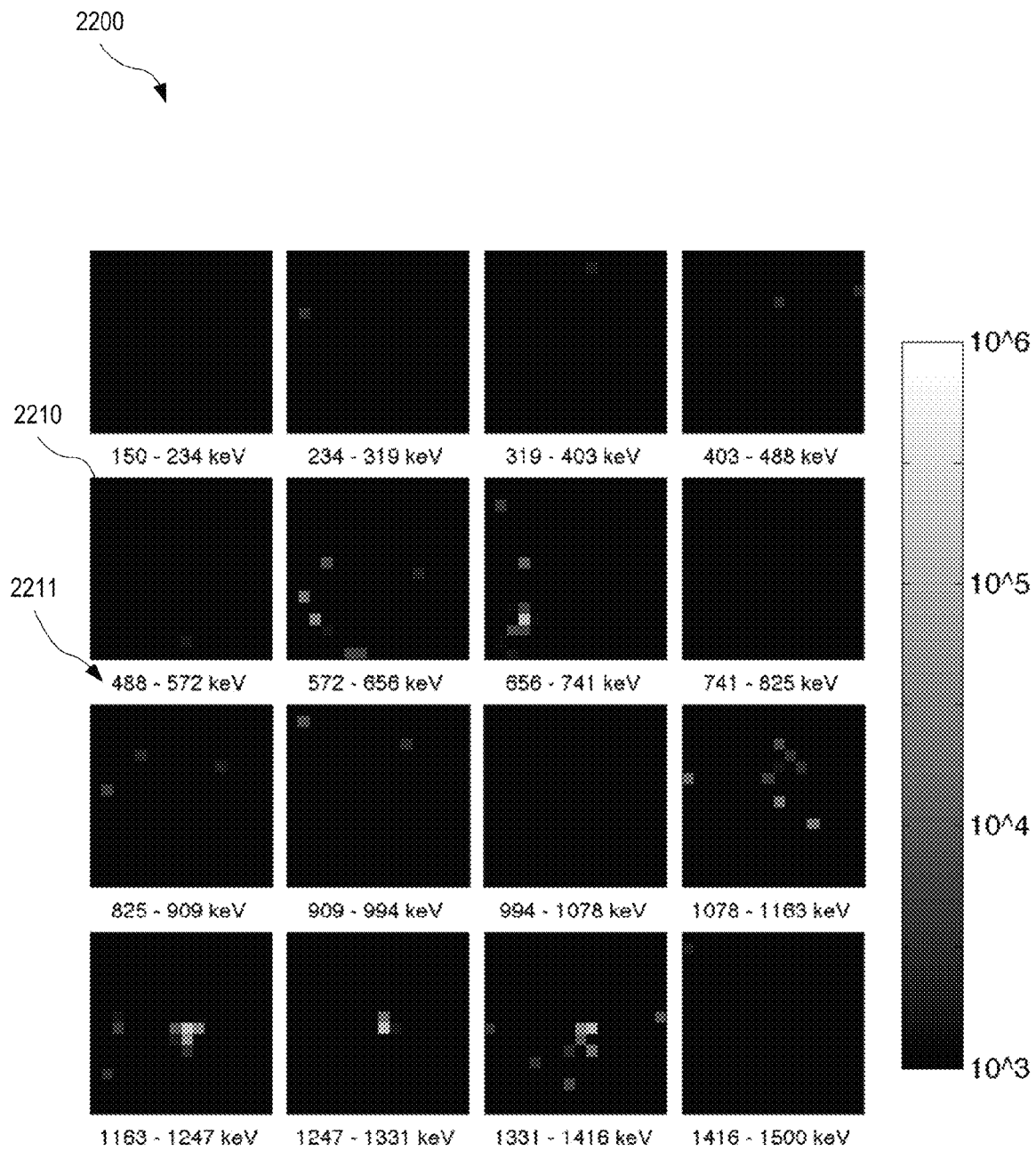
FIG. 22 shows image reconstruction results for two point sources viewed by the gamma ray imaging system of FIG. 1, obtained using the image reconstruction method of FIG. 9, according to an embodiment.

FIG. 22 shows a reconstructed image 2200 of two point sources, a 640 mCi ($2.37 \times 10^{10}$ Bq) $^{137}$Cs source at 662 keV, and a 340 mCi ($1.26 \times 10^{10}$ Bq) $^{60}$Co source with energies 1173 and 1332 keV. The point sources were at a distance of 100 m from gamma ray imaging system 110 (FIGS. 1 and 2). The simulation included natural background. Reconstructed image 2000 is shown as a series of sub-images 2210 for a respective series of energy bins 2211. The energy flux scale displayed is logarithmic, spanning a three decade range, from $10^3$ to $10^6$ keV per spatial bin of the object space.

Assuming a 10 minute data acquisition time, 104 photons were detected in Compton scattering layer 150 (FIGS. 1 and 2) from the $^{137}$Cs source. 104 photons, evenly split between the two energies, were detected in Compton scattering layer 150 (FIGS. 1 and 2) from the $^{60}$Co source. The $^{137}$Cs source is located in the lower left corner of sub-images 2210 and, while the $^{60}$Co source is found in the center. Both sources are easily identified in reconstructed image 2200. Due to the proximity of the source energies to the chosen energy bin boundaries, the signals in the neighboring energy bins are expected.

Changes may be made in the above methods and systems without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present method and system, which, as a matter of language, might be said to fall therebetween.

What is claimed is:

1. A system for imaging at least one gamma source, comprising:
   a pixelated Compton scattering layer for producing scattered gamma photons from Compton scattering of gamma photons emitted by the gamma source; and
   a non-pixelated full-energy detector for detecting at least a portion of the scattered gamma photons geometrically encoded by a coded aperture located at a distance from the pixelated Compton scattering layer and positioned between the pixelated Compton scattering layer and the full-energy detector.

2. The system of claim 1, the aperture comprising a plurality of apertures, for transmitting the scattered gamma photons, the plurality of apertures being configured in a position-dependent pattern to provide geometrical information about the propagation of the scattered gamma photons transmitted by the coded aperture.

3. The system of claim 2, the thickness of the non-pixelated full-energy detector being configured to absorb the full energy of substantially all scattered gamma photons incident thereupon.

4. The system of claim 2, the pixelated Compton scattering layer being one unit square in area, and the distance being between 0.2 and 0.8 units.

5. The system of claim 1, further comprising a data processing system, communicatively coupled to the pixelated Compton scattering layer and the non-pixelated full-energy detector, for determining an image of the one or more gamma sources from data generated by the pixelated Compton scattering layer and the non-pixelated full-energy detector.

6. The system of claim 5, the data being a plurality of coincidence data, each of the coincidence data comprising location and Compton energy shift of a Compton scattering event in the pixelated Compton scattering layer, and energy of a scattered gamma photon produced in the Compton scattering, the location and Compton energy shift being measured by the pixelated Compton scattering layer, and the energy being measured by the non-pixelated full-energy detector.

7. The system of claim 5, the image comprising:
angular location and extent of the one or more gamma sources within a field of view; and
energy of the gamma photons emitted by the one or more gamma sources.

8. The system of claim 5, the image comprising:
three-dimensional location and extent of the one or more gamma sources; and
energy of the gamma photons emitted by the one or more gamma sources.

9. The system of claim 5, the data processing system comprising machine-readable instructions for determining the image, the instructions comprising a plurality of probabilities, each probability being the probability of a set of events in the pixelated Compton scattering layer and the non-pixelated full-energy detector being generated by a gamma source configuration.

10. The system of claim 9, the instructions further comprising instructions for determining the plurality of probabilities.

11. The system of claim 10, the plurality of probabilities being associated with a resolution and configuration of at least a portion of a field of view, and determining the plurality of probabilities comprising determining the probabilities associated with an optimal resolution and configuration.

12. The system of claim 9, the data processing system further comprising a processor communicatively coupled to the instructions for executing the instructions to determine the image.

13. The system of claim 1, further comprising:
first electronic circuitry coupled to the pixelated Compton scattering layer for generating first signals indicating position and Compton energy shift of Compton scattering events producing the scattered gamma photons; and
second electronic circuitry coupled to the non-pixelated full energy detector for generating second signals indicating the energy of the at least a portion of the scattered photons transmitted by the aperture.

14. The system of claim 13, further comprising a data processing system comprising:
a signal processing unit for processing the first and second signals to generate coincidence data for first and second signals originating from same Compton scattering event, the coincidence data comprising the position of the Compton scattering event, the Compton energy shift, and energy of the scattered gamma photon; and
a memory, communicatively coupled to the signal processing unit, for storage of the coincidence data.

15. The system of claim 14, the data processing system further comprising a data analysis module for determining an image of the one or more gamma sources from the coincidence data.

16. The system of claim 15, the data analysis module comprising:
machine-readable instructions comprising (a) a plurality of probabilities, each probability being the probability of a set of events in the pixelated Compton scattering layer and the non-pixelated full-energy detector being generated by a gamma source configuration, and (b) image reconstruction instructions; and
a processor for executing the image reconstruction instructions, using the plurality of probabilities, to determine the image.

17. A method for imaging at least one gamma source, comprising:
detecting a plurality of coincidence events, each of the coincidence events comprising (a) Compton scattering of a gamma photon in a pixelated Compton scattering layer, the gamma photon being emitted by the gamma source, and (b) transmission of a scattered gamma photon to a non-pixelated full-energy detector, the scattered gamma photon being produced in the Compton scattering and transmitted through a coded aperture located at a distance from the pixelated Compton scattering layer; and
determining an image of the gamma source from the detection of the plurality of coincidence events.

18. The method of claim 17,
further comprising measuring, for each of the coincidence events, coincidence data comprising the location and Compton energy shift of the Compton scattering and the energy of the scattered gamma photon; and
in the step of determining, the image being determined from the plurality of coincidence data.

19. The method of claim 18, the image being the most probable solution based on a plurality of probabilities, each probability being the probability of a set of coincidence data being generated by a gamma source configuration.

20. The method of claim 19, further comprising calculating the plurality of probabilities.

21. The method of claim 20, calculating comprising performing a Monte Carlo simulation.

22. The method of claim 17, the image comprising:
angular location and extent of the gamma source within a field of view; and
energy of the gamma photons emitted by the gamma source.

23. The method of claim 17, the image comprising:
three-dimensional location and extent of the gamma source; and
energy of the gamma photons emitted by the gamma source.

24. The method of claim 20, the plurality of probabilities being associated with a resolution and configuration of a measurement field.

25. The method of claim 24, comprising:
determining a first image of the gamma source using a first plurality of probabilities being associated with a first resolution and first configuration; and
determining a second image of the gamma source using a second plurality of probabilities being associated with a second resolution and second configuration, the second resolution and the second configuration being determined from the first image.

* * * * *